(12) United States Patent
Norris et al.

(10) Patent No.: US 10,877,040 B1
(45) Date of Patent: Dec. 29, 2020

(54) IMAGING MASS SPECTROMETRY AND USES THEREOF

(71) Applicant: Frontier Diagnostics, LLC, Smyrna, TN (US)

(72) Inventors: Jeremy L. Norris, Smryna, TN (US); Richard M. Caprioli, Brentwood, TN (US); Jason B. Robbins, Nashville, TN (US)

(73) Assignee: FRONTIER DIAGNOSTICS, LLC, Smyrna, TN (US)

( * ) Notice: Subject to any disclaimer, the term of this patent is extended or adjusted under 35 U.S.C. 154(b) by 0 days.

(21) Appl. No.: 16/397,690

(22) Filed: Apr. 29, 2019

Related U.S. Application Data

(63) Continuation-in-part of application No. PCT/US2017/058996, filed on Oct. 30, 2017.

(60) Provisional application No. 62/414,327, filed on Oct. 28, 2016.

(51) Int. Cl.
| | |
|---|---|
| *H01J 49/00* | (2006.01) |
| *G01N 33/574* | (2006.01) |
| *G01N 33/68* | (2006.01) |
| *C12Q 1/6886* | (2018.01) |

(52) U.S. Cl.
CPC ....... *G01N 33/5743* (2013.01); *C12Q 1/6886* (2013.01); *G01N 33/6848* (2013.01); *C12Q 2600/112* (2013.01); *C12Q 2600/158* (2013.01)

(58) Field of Classification Search
CPC .... H01J 49/00; H01J 49/0027; H01J 49/0031; H01J 49/02; G01N 33/57
USPC ............................................... 250/281, 282
See application file for complete search history.

(56) References Cited

U.S. PATENT DOCUMENTS

| | | | |
|---|---|---|---|
| 5,757,994 A | 5/1998 | Schoenwald et al. | |
| 5,788,166 A | 8/1998 | Valaskovic et al. | |
| 5,838,002 A | 11/1998 | Sheehan | |
| 5,986,258 A | 11/1999 | Park | |
| 8,822,159 B2 | 9/2014 | Caprioli et al. | |
| 2009/0208921 A1* | 8/2009 | Tempst | C12Q 1/56 435/4 |
| 2016/0126073 A1* | 5/2016 | Norris | H01J 49/0004 250/282 |
| 2017/0154759 A1* | 6/2017 | Lazova | H01J 49/0036 |

FOREIGN PATENT DOCUMENTS

AU  2016210732  8/2016

OTHER PUBLICATIONS

Steurer et al., MALDI Mass Spectrometric Imaging Based Identification of Clinically Relevant Signals in Prostate Cancer Using Large-Scale Tissue Microarrays, 2013, Int. J. Cnacer: 133, pp. 920-928. (Year: 2013).*
Abbondanzo, Susan L. "Paraffin immunohistochemistry as an adjunct to hematopathology." Annals of diagnostic pathology 3.5 (1999): 318-327.
Bahr, U., et al. "Delayed extraction time-of-flight MALDI mass spectrometry of proteins above 25000 Da." Journal of mass spectrometry 32.10 (1997): 1111-1116.

(Continued)

*Primary Examiner* — Jason L McCormack
(74) *Attorney, Agent, or Firm* — Baker Donelson

(57) ABSTRACT

The present invention is directed to a mass spectrometry approach to identifying non-Spitzoid melanoma, and distinguishing non-Spitzoid nevi from non-Spitzoid malignant melanoma.

20 Claims, 7 Drawing Sheets

(56) References Cited

OTHER PUBLICATIONS

Bentzley, Catherine M., et al. "Oligonucleotide sequence and composition determined by matrix-assisted laser desorption/ionization." Analytical chemistry 68.13 (1996): 2141-2146.

Caprioli, Richard M., Terry B. Farmer, and Jocelyn Gile. "Molecular imaging of biological samples: localization of peptides and proteins using MALDI-TOF MS." Analytical chemistry 69.23 (1997): 4751-4760.

Chaurand, Pierre, Markus Stoeckli, and Richard M. Caprioli. "Direct profiling of proteins in biological tissue sections by MALDI mass spectrometry." Analytical chemistry 71.23 (1999): 5263-5270.

Desiderio, Dominic M. "Mass spectrometric quantification of neuropeptides." Protein and Peptide Analysis by Mass Spectrometry. Humana Press, 1996. 57-65.

Desiderio, Dominic M., et al. "Matrix-assisted laser desorption/ionization mass spectrometric quantification of the mu opioid receptor agonist DAMGO in ovine plasma." Journal of mass spectrometry 35.6 (2000): 725-733.

Duncan, Mark W., Gabrijela Matanovic, and Anne Cerpa-Poljak. "Quantitative analysis of low molecular weight compounds of biological interest by matrix-assisted laser desorption ionization." Rapid Communications in Mass Spectrometry 7.12 (1993): 1090-1094.

Faulstich, Konrad, et al. "A sequencing method for RNA oligonucleotides based on mass spectrometry." Analytical chemistry 69.21 (1997): 4349-4353.

Ferrara et al, "Spitz Nevus, Spitz Tumor, and Spitzoid Melanoma : A Comprehensive Clinicopathologic Overview," Dermatol Clin. Oct. 2013;31(4):589-98.

Gerami, P., Beilfuss, B., Haghighat, Z., Fang, Y., Jhanwar, S., and Busam, K. J. (2011) Fluorescence in situ hybridization as an ancillary method for the distinction of desmoplastic melanomas from sclerosing melanocytic nevi, J Cutan Pathol 38, 329-334.

Gerami, P., Jewell, S. S., Morrison, L. E., Blondin, B., Schulz, J., Ruffalo, T., Matushek, P. t, Legator, M., Jacobson, K., Dalton, S. R., Charzan, S., Kolaitis, N. A., Guitart, J., Lertsbarapa, T., Boone, S., LeBoit, P. E., and Bastian, B. C. (2009) Fluorescence in situ hybridization (FISH) as an ancillary diagnostic tool in the diagnosis of melanoma, Am J Surg Pathol 33, 1146-1156.

Gobom, Johan, et al. "Detection and quantification of neurotensin in human brain tissue by matrix-assisted laser desorption/ionization time-of-flight mass spectrometry." Analytical chemistry 72.14 (2000): 3320-3326.

Horak, Jeannie, Wolfgang Werther, and Erich R. Schmid. "Optimisation of the quantitative determination of chlormequat by matrix-assisted laser desorption/ionisation mass spectrometry." Rapid Communications in Mass Spectrometry 15.4 (2001): 241-248.

Jespersen, Sonja, et al. "Direct Sequencing of Neuropeptides in Biological Tissue by MALDI-PSD Mass Spectrometry." Analytical chemistry 71.3 (1999): 660-666.

Jiang, Gaosong, and Thava Vasanthan. "MALDI-MS and HPLC quantification of oligosaccharides of lichenase-hydrolyzed water-soluble β-glucan from ten barley varieties." Journal of agricultural and food chemistry 48.8 (2000): 3305-3310.

Li, Lingjun, Rebecca W. Garden, and Jonathan V. Sweedler. "Single-cell MALDI: a new tool for direct peptide profiling." Trends in biotechnology 18.4 (2000): 151-160.

Lovelace, Jerry Lee, Jozef J. Kusmierz, and Dominic M. Desiderio. "Analysis of methionine enkephalin in human pituitary by multi-dimensional reversed-phase high-performance liquid chromatography, radioreceptor assay, radioimmunoassay, fast atom bombardment mass spectrometry, and mass spectrometry—mass spectrometry." Journal of Chromatography B: Biomedical Sciences and Applications 562.1-2 (1991): 573-584.

Lynn, Eric C., et al. "Identification of Enterobacteriaceae bacteria by direct matrix-assisted laser desorptiom/ionization mass spectrometric analysis of whole cells." Rapid communications in mass spectrometry 13.20 (1999): 2022-2027.

Massi, G., Leboit, P. (2004) Histological Diagnosis of Nevi and Melanoma, Springer Verlag, Berlin.

Miketova, Petra, and Karl H. Schram. "Mass spectrometry of nucleotides and oligonucleotides." Molecular biotechnology 8.3 (1997): 249-253.

Mirgorodskaya, Olga A., et al. "Quantitation of peptides and proteins by matrix-assisted laser desorption/ionization mass spectrometry using 18O-labeled internal standards." Rapid Communications in Mass Spectrometry 14.14 (2000): 1226-1232.

Muddiman, David C., et al. "Characterization of PCR products from bacilli using electrospray ionization FTICR mass spectrometry." Analytical Chemistry 68.21 (1996): 3705-3712.

Nelson, Randall W., et al. "Mass determination of human immunoglobulin IgM using matrix-assisted laser desorption/ionization time-of-flight mass spectrometry." Rapid Communications in Mass Spectrometry 8.8 (1994): 627-631.

Nguyen, D. N., G. W. Becker, and R. M. Riggin. "Protein mass spectrometry: applications to analytical biotechnology." Journal of Chromatography A 705.1 (1995): 21-45.

Takach, Edward J., et al. "Accurate mass measurements using MALDI-TOF with delayed extraction." Journal of protein chemistry 16.5 (1997): 363-369.

Troxel, D. B., and Sabella, J. D. (1994) Problem areas in pathology practice. Uncovered by a review of malpractice claims, Am J Surg Pathol 18, 821-831.

Wittmann, Christoph, and Elmar Heinzle. "Application of MALDI-TOF MS to lysine-producing Corynebacterium glutamicum: A novel approach for metabolic flux analysis." European journal of biochemistry 268.8 (2001): 2441-2455.

Wittmann, Christoph, and Elmar Heinzle. "MALDI-TOF MS for quantification of substrates and products in cultivations of Corynebacterium glutamicum." Biotechnology and bioengineering 72.6 (2001): 642-647.

Wu, Jiangyue, et al. "An automated MALDI mass spectrometry approach for optimizing cyclosporin extraction and quantitation." Analytical chemistry 69.18 (1997): 3767-3771.

Yang, Youjun, et al. "Mechanism of inhibition of the class A β-lactamases PC1 and TEM-1 by tazobactam Observation of reaction products by electrospray ionization mass spectrometry." Journal of Biological Chemistry 275.35 (2000): 26674-26682.

Zhong, Ling, Roy Eisenhandler, and Kuang C. Yeh. "Determination of famotidine in low-volume human plasma by normal-phase liquid chromatography/tandem mass spectrometry." Journal of Mass spectrometry 36.7 (2001): 736-741.

Zweigenbaum, J. A., et al. "Direct analysis of microcystins by microbore liquid chromatography electrospray ionization ion-trap tandem mass spectrometry." Journal of pharmaceutical and biomedical analysis 23.4 (2000): 723-733.

Zweigenbaum, Jerry, et al. "High-throughput bioanalytical LC/MS/MS determination of benzodiazepines in human urine: 1000 samples per 12 hours." Analytical chemistry 71.13 (1999): 2294-2300.

Muddiman, David C., et al. "Charge-state reduction with improved signal intensity of oligonucleotides in electrospray ionization mass spectrometry" Journal of the American Society for Mass Spectrometry 7.8 (1996): 697-706.

Lee, D et al. "Are all Melanomas the Same", Jan. 18, 2016; American Cancer Society; vol. 106, No. 4, p. 907-913.

PCT/US17/58996 International Search Report dated Jan. 17, 2018.

PCT/US17/58996 Written Opinion of ISA dated Jan. 17, 2018.

(2012) Cancer Facts and Figures, The American Cancer Society.

Allen, J.L. et al. May 20-24, 2012. A Molecular Examination of Benign and Malignant Melanocytic Tumors by Histology-Directed Tissue Profiling. Proceedings of the 60th ASMS Conference on Mass Spectrometry and Allied Topics, Vancouver, BC.

Alomari, A., et al. Jan. 20, 2015. Congenital nevi versus metastatic melanoma in a newborn to a mother with malignant melanoma—diagnosis supported by sex chromosome analysis and Imaging Mass Spectrometry. J Cutan Pathol.,42(10):757-64.

Bastian, B. C, Olshen, A. B., LeBoit, R E., and Rinkel, D. (2003) Classifyingmelanocytic tumors based on DNA copy number changes, Am J Pathol 163, 1765-1770.

Bauer, Jürgen, and Boris C, Bastian. "Distinguishing melanocytic nevi from melanoma by DNA copy number changes: comparative genomic hybridization as a research and diagnostic tool." Dermatologic therapy 19.1 (2006): 40-49.

(56) References Cited

OTHER PUBLICATIONS

Bucknall, Martin, Kim YC Fung, and Mark W. Duncan. "Practical quantitative biomedical applications of MALDI-TOF mass spectrometry." Journal of the American Society for Mass Spectrometry 13.9 (2002): 1015-1027.
Casadonte, Rita, and Richard M. Capriole. "Proteomic analysis of formalin-fixed paraffin-embedded tissue by MALDI imaging mass spectrometry." Nature protocols 6.11 (2011): 1695.
Chaurand, P., F. Luetzenkirchen, and B. Spengler. "Peptide and protein identification by matrix-assisted laser desorption ionization (MALDI) and MALDI-post-source decay time-of-flight mass spectrometry." Journal of the American Society for Mass Spectrometry 10.2 (1999): 91-103.
Gaiser, T., Kutzner, H., Palmedo, G, Siegelin, M. D., Wiesner, T., Bruckner, T., Hartschuh, W., Enk, A. H., and Becker, M. R. (2010) Classifying ambiguous melanocytic lesions with FISH and correlation with clinical long-term follow up, Mod Pathol 23, 413-419.
Gerami, P., and Zembowicz, A. (2011) Update on fluorescence in situ hybridization in melanoma: state of the art, Arch Pathol Lab Med 135, 830-837.
Hardesty, W. and Caprioli, R., Jun. 2008. In situ imaging of proteins in tissues using mass spectrometry. Anal. Bioanal. Chem.; 391(3):899-903.
Hardesty, W. et al. Jun. 10, 2011. Protein signatures for survival and recurrence in metastatic melanoma. J. Proteomics.; 74(7):1002-14.
Hardesty, WM. Dec. 2010. Proteornic Analysis and Classification of Metastatic Melanoma by MALDI Imaging Mass Spectrometry. PhD thesis, Vanderbilt University, https://etd.library.vanderbilt.edu/availabl/etd-08252010-081820.
James, et al. 2013. An introduction to statistical learning. New York: Springer.
Kanazawa, Koki, et al. "Establishment of a method for mapping of N-linked oligosaccharides and its use to analyze industrially produced recombinant erythropoietin." Biological and Pharmaceutical Bulletin 22.4 (1999): 339-346.
Lazova, R., Apr. 15-17, 2013. Imaging mass spectrometry—A novel ancillary method for the diagnosis of malignant melanoma. J. Clin. Exp. Dermatol. Res., 4:2.
Lazova, R., et al. (2016) Imaging mass spectrometry assists in the classification of diagnostically challenging atypical Spitzoid neoplasms. J AmAcad Dermatol, pii: S0190-9622 (16): 30483-2.
Lazova, R., et al. Feb. 2012. Imaging Mass Spectrometry—a new promising method to differentiate Spitz nevi from Spitzoid malignant melanomas, Am J Dermatopathol.; 34(1):82-90.
Lazova, R., Seeley, E. H., Keenan, M., Guemrguieeva, R., Caprioli, R. M., (2012) Imaging Mass Spectrometry—a new and promising method to differentiate Spitz nevi from Spitzoid malignant melanomas. Am J Dermatopathol, 34 (I):82-90.
Marie, A., F. Fournier, and J. C. Tabet. "Characterization of synthetic polymers by MALDI-TOF/MS: Investigation into new methods of sample target preparation and consequence on mass spectrum finger print." Analytical chemistry 72.20 (2000): 5106-5114.

Morgan, T. M., Seeley, E. H., Fadare, O., Caption, R. M., and Clark, P. E. (2013) Imaging the clear cell renal cell carcinoma proteome, J Urol 189, 1097-1103.
Norris, J. L., and Caprioli, R. M. (2013) Analysis of tissue specimens by matrix-assisted laser desorption/ionization imaging mass spectrometry in biological and clinical research, Chem Rev 113, 2309-2342.
Norris. J. L., Caprioli, R. M., (2013) Imaging Mass Spectrometry: A New Tool for Pathology in a Molecular Age. Proteomics Clin. Appl. 7 (11-12):733-8.
Norris, J.L.; Tsui, T. ; Gutierrez, D.B.: Caprioli, R.M. (2016) Pathology interface for the molecular analysis of tissue by mass spectrometry. J Pathol Inform. 2016 7: 13.
Poole, C. (2014) The Cost of Melanoma: Early Detection Could Save Millions of Lives, Melanoma International Foundation.
Robboy, S J., Weintraub, S., Horvath, A. E., Jensen, B. W., Alexander, C. B., Fody, E. P., Crawford, J. M., Clark, J. R., Cantor-Weinberg, J., Joshi, M. G, Cohen, M. B., Prystowsky, M. B., Bean, S. M., Gupta, S., Powell, S. Z., Speights, V. O., Jr., Gross, D. J., and Black-Schaffer, W. S. (2013) Pathologist workforce in the United States: I. Development of a predictive model to examine factors influencing supply, Archives of pathology & laboratory medicine 137, 1723-1732.
Sabel. M. S., Liu, Y., Lubman, D. M., (2011) Proteomics in Melanoma Biomarker Discovery: Great Potential, Many Obstacles. Int J Proteomics. 2011 : 181890.
Stoeckli, Markus, et al. "Imaging mass spectrometry: a new technology for the analysis of protein expression in mammalian tissues." Nature medicine 7.4 (2001): 493.
Taguchi, F., Solomon, B., Gregorc, V., Roder, H., Gray, R,, Kasahara, K., Nishio, M., Brahmer, J., Spreafico, A., Ludovini, V., Massion, P. P., Dziadziuszko, R., Schiller, J., Grigorieva, J., Tsypin, M., Hunsucker, S. W Caprioli, R., Duncan, M. W., Hirsch, F. R., Bunn, P. A., Jr., and Carbone, D. P. (2007) Mass spectrometry to classify non-small-cell lung cancer patients for clinical outcome after treatment with epidermal growth factor receptor tyrosine kinase inhibitors: a muiticohort cross-institutional study, J Natl Cancer Inst 99, 838-846.
Veenhuizen, K. C, De Wit, P. E., Mooi, W J., Scheffer, E., Verbeek, A. L., and Ruiter, D. J. (1997) Quality assessment by expert opinion in melanoma pathology, experience of the pathology panel of the Dutch Melanoma Working Party, J Pathol 182, 266-272.
Vergier, B., ProchazKova-Carlotti, M., de la Fouchardiere, A., Cerroni, L., Massi, D., De Giorgi, V., Bailly, C, Wesselmann, U., Kariseiadze, A., Avril, M. F., Jouary, T., and Merlio, J. P. (2011) Fluorescence in situ hybridization, a diagnostic aid in ambiguous melanocytic tumors: European study of 113 cases, Mod Pathol 24, 613-623.
Vrana, J. A., Gamez, J. D., Madden, B. J., Theis, J. D., Bergen, H. R., 3rd, and Dogan, A. (2009) Classification of amyloidosis by laser microdissection and mass spectrometry-based protecmic analysis in clinical biopsy specimens, Blood 114, 4957-4959.

\* cited by examiner

| 25 PEAKS USED IN THE SVM CLASSIFER REPORTED IN THE POSTER ||
|---|---|
| MASS | WEIGHT |
| 1954.9 | 1.11 |
| 1199.0 | 1.00 |
| 1184.9 | 0.91 |
| 1411.8 | 0.90 |
| 2216.3 | 0.89 |
| 1791.7 | 0.87 |
| 914.6 | 0.85 |
| 2636.5 | 0.83 |
| 1429.1 | 0.82 |
| 1629.8 | 0.82 |
| 3017.6 | 0.81 |
| 1491.9 | 0.73 |
| 734.4 | 0.73 |
| 1132.7 | 0.70 |
| 1985.1 | 0.69 |
| 1488.0 | 0.69 |
| 872.4 | 0.68 |
| 1167.8 | 0.68 |
| 1194.8 | 0.66 |
| 1120.6 | 0.66 |
| 1127.6 | 0.66 |
| 1243.8 | 0.65 |
| 2105.3 | 0.64 |
| 1495.9 | 0.62 |
| 1466.9 | 0.62 |

FIG. 6

| MASS | WILCOXON (p-VALUE) | MASS | WILCOXON (p-VALUE) | MASS | WILCOXON (p-VALUE) | MASS | WILCOXON (p-VALUE) | MASS | WILCOXON (p-VALUE) | MASS | WILCOXON (p-VALUE) |
|---|---|---|---|---|---|---|---|---|---|---|---|
| 1199 | 1.74E-06 | 2455.27 | 0.014 | 852.5 | 0.14 | 1095.44 | 0.293 | 1046.38 | 0.531 | 3339.52 | 0.837 |
| 1184.87 | 1.74E-06 | 2870.96 | 0.0145 | 1116.93 | 0.142 | 2762.33 | 0.293 | 901.58 | 0.531 | 715.3 | 0.838 |
| 1194.76 | 3.17E-06 | 795.42 | 0.0163 | 1491.94 | 0.142 | 985.6 | 0.293 | 764.44 | 0.542 | 857.56 | 0.838 |
| 2636.51 | 7.09E-06 | 1303.82 | 0.0223 | 1154.8 | 0.147 | 1128.67 | 0.324 | 1970.07 | 0.549 | 1524.72 | 0.838 |
| 1954.89 | 0.0000239 | 2960.81 | 0.0228 | 3086.21 | 0.166 | 836.59 | 0.329 | 3102.46 | 0.549 | 666.08 | 0.849 |
| 2105.34 | 0.0000298 | 2216.29 | 0.0228 | 1837.71 | 0.172 | 1187.77 | 0.329 | 1341.63 | 0.56 | 1235.75 | 0.855 |
| 1669.82 | 0.0000491 | 2706.38 | 0.0228 | 1962.82 | 0.182 | 1988.89 | 0.35 | 1125.73 | 0.571 | 1352.83 | 0.855 |
| 1629.81 | 0.0000906 | 3070.09 | 0.0237 | 1338.9 | 0.182 | 643.99 | 0.365 | 1163.74 | 0.599 | 3350.4 | 0.867 |
| 976.57 | 0.000552 | 2424.38 | 0.0247 | 3184.72 | 0.188 | 3399.6 | 0.414 | 831.51 | 0.601 | 788.48 | 0.873 |
| 2951.84 | 0.000753 | 914.57 | 0.0368 | 2690.65 | 0.202 | 2812.29 | 0.414 | 1481.74 | 0.601 | 1250.78 | 0.873 |
| 1335.82 | 0.000928 | 1111.79 | 0.0432 | 1651.74 | 0.209 | 1297.86 | 0.424 | 758.43 | 0.601 | 1032.73 | 0.873 |
| 1280.87 | 0.00094 | 1460.18 | 0.0477 | 1060.24 | 0.241 | 840.54 | 0.43 | 664.3 | 0.629 | 919.58 | 0.873 |
| 1068.69 | 0.00106 | 898.6 | 0.0495 | 2773.93 | 0.241 | 679.42 | 0.43 | 1321.48 | 0.636 | 1349.92 | 0.885 |
| 1791.74 | 0.00119 | 2116.32 | 0.0533 | 1127.62 | 0.241 | 1173.73 | 0.436 | 3382.94 | 0.636 | 1543.69 | 0.896 |
| 1243.77 | 0.00163 | 1132.68 | 0.0533 | 2498.45 | 0.241 | 1129.61 | 0.436 | 1702.83 | 0.645 | 1606.83 | 0.913 |
| 1138.84 | 0.00167 | 1586.8 | 0.062 | 1506.11 | 0.259 | 1563.84 | 0.438 | 647.99 | 0.645 | 1124.71 | 0.913 |
| 1466.87 | 0.00173 | 1411.8 | 0.0804 | 1028.7 | 0.259 | 2789.11 | 0.438 | 3638.07 | 0.645 | 2191 | 0.913 |
| 1429.14 | 0.00179 | 1143.7 | 0.0828 | 616.54 | 0.259 | 1959.06 | 0.444 | 963.5 | 0.656 | 628.14 | 0.918 |
| 1384.75 | 0.00185 | 1167.83 | 0.0828 | 1126.61 | 0.274 | 1821.88 | 0.454 | 1242.75 | 0.68 | 868.53 | 0.918 |
| 1203.71 | 0.00356 | 1105.76 | 0.0828 | 941.49 | 0.274 | 871.02 | 0.465 | 833.06 | 0.68 | 1189.63 | 0.918 |
| 1262.64 | 0.00369 | 1563.16 | 0.0905 | 2781.1 | 0.281 | 1212.71 | 0.475 | 890.35 | 0.686 | 649.98 | 0.94 |
| 3054.41 | 0.00454 | 872.41 | 0.0936 | 607.67 | 0.282 | 1161.68 | 0.501 | 631.99 | 0.686 | 1079.49 | 0.94 |
| 1487.98 | 0.00511 | 1120.64 | 0.0969 | 1325.99 | 0.282 | 842.57 | 0.511 | 1906.94 | 0.693 | 866.41 | 0.967 |
| 1495.89 | 0.00532 | 1744.12 | 0.106 | 1299.98 | 0.282 | 1229.79 | 0.518 | 944.63 | 0.693 | 691.96 | 0.967 |
| 1985.07 | 0.00649 | 1155.64 | 0.115 | 987.58 | 0.29 | 1101.67 | 0.518 | 2993.54 | 0.705 | 713.2 | 0.987 |
| 1715.81 | 0.00853 | 1014.42 | 0.131 | 1414.85 | 0.291 | 1090.55 | 0.529 | 1353.83 | 0.712 | 606.01 | 0.987 |
| 2088.35 | 0.0116 | 734.38 | 0.135 | 855.1 | 0.291 | 717.39 | 0.529 | 701.38 | 0.712 | 2799.92 | 1 |
| 3017.58 | 0.0116 | 906.14 | | 1267.97 | 0.291 | 1764.25 | | 957.89 | | | |
| 1777.24 | 0.0116 | 1477.88 | | 1359.72 | | 1557.74 | | 630.01 | | | |
| 1825.68 | 0.0116 | 1240.91 | | 1367.02 | | 1616.69 | | | | | |

IMAGING MASS SPECTROMETRY AND USES THEREOF

This application is a Continuation in Part of International Application PCT/US2017/058996, filed on Oct. 30, 2017, which claims priority from U.S. Provisional Application No. 62/414,327 filed on Oct. 28, 2016, the entire contents of each which are incorporated herein by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

The present invention is directed to methods for identifying non-Spitzoid melanoma, and distinguishing the same from non-Spitzoid nevi.

BACKGROUND OF THE INVENTION

Melanoma is a malignant tumor of melanocytes. Melanocytes produce the dark pigment, melanin, which is responsible for the color of skin. These cells predominantly occur in skin, but are also found in other parts of the body, including the bowel and the eye (see uveal melanoma).

Melanoma can originate in any part of the body that contains melanocytes. Melanoma is less common than other skin cancers. However, it is much more dangerous if it is not found early. It causes the majority (75%) of deaths related to skin cancer. Worldwide, doctors diagnose about 160,000 new cases of melanoma yearly. It is more common in women than in men. In women, the most common site is the legs and melanomas in men are most common on the back. It is particularly common among Caucasians, especially northwestern Europeans living in sunny climates. There are high rates of incidence in Oceania, Northern America, Europe, southern Africa, and Latin America, with a paradoxical decrease in southern Italy and Sicily. This geographic pattern reflects the primary cause, ultraviolet light (UV) exposure crossed with the amount of skin pigmentation in the population.

According to a WHO report, about 48,000 melanoma related deaths occur worldwide per year. The treatment includes surgical removal of the tumor. If melanoma is found early, while it is still small and thin, and if it is completely removed, then the chance of cure is high. The likelihood of the melanoma coming back or spreading depends on how deeply it has gone into the layers of the skin. For melanomas that come back or spread, treatments include chemo- and immunotherapy, or radiation therapy.

SUMMARY OF THE INVENTION

An aspect of the present invention provides a method of differentiating non-Spitzoid nevus from non-Spitzoid malignant melanoma comprising subjecting a sample from a subject to mass spectrometry; obtaining a mass spectrometric profile from said sample; comparing said sample mass spectrometric profile to a profile obtained from a known normal, non-Spitz nevus and/or non-Spitzoid malignant melanoma sample; and identifying said lesion as a non-Spitz nevus or non-Spitzoid malignant melanoma based on the similarities and differences between said mass spectrometric profile and said known mass spectrometric profile(s). In embodiments, the similarity of the sample from the subject to a known profile, such as a known molecular profile, is determined using a statistical or machine learning algorithm. Non-limiting examples of the machine learning algorithm comprise a genetic algorithm, support vestor machine, or supervised neural network. In embodiments, the sample comprises a skin lesion sample, such as those with melanocytic components, stromal components, or a combination thereof. In other embodiments, the sample comprises any desired bodily tissue, non-limiting examples of which comprise blood, serum, cerebrospinal fluid, urine, sweat, saliva, skin, skin punches, or solid tissue biopsies. In embodiments, the mass spectrometric profile comprises one or more peaks at about m/z 1955, about m/z 1199, about m/z 1184, about m/z 1412, or about m/z 2216. In other embodiments, the mass spectrometric profile comprises one or more peaks at about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9. In embodiments, the mass spectrometric profile is also known as the molecular profile. In embodiments, the mass spectrometric profile comprises one molecule or a plurality of molecules. Non-limiting examples of types of molecules represented in the mass spectrometric profile comprise proteins, peptides, lipid, metabolites, nucleic acids or a combination thereof. In embodiments, the methods as described herein can further comprise the step of administering to the subject an effective amount of an anti-cancer agent. Non-limiting examples of such agents comprise chemotherapy, immunotherapy, toxin therapy, radiotherapy, or a combination thereof. In embodiments, non-limiting examples of mass spectrometry comprise secondary ion mass spectrometry, laser desorption mass spectrometry, matrix assisted laser desorption/ionization mass spectrometry, electrospray mass spectrometry, or desorption electrospray ionization. In embodiments, the methods as described herein can further comprise the step of obtaining a sample from said subject. For example, the subject can be a mammalian subject, for example, a human subject, such as one at risk of non-Spitzoid melanoma. In some embodiments, the mammal can be a canine, feline, or equine. In this example, a tissue sample can be obtained from the subject, and tested for biomarkers of melanoma using methods as described herein. The tissue can be obtained using methods known in the art. In embodiments, methods as described herein can further comprise the step of performing a mass spectrometric analysis of a known non-Spitz nevi, a known non-Spitzoid malignant melanoma lesion, or a combination thereof. For example, the known non-Spitzoid nevi or the known non-Spitzoid malignant melanoma lesion can be obtained from the subject whose sample tissue is being tested using embodiments and methods as described herein. In embodiments, the methods as described herein can further comprise performing histologic analysis on the tissue sample. Further, embodiments as described herein can also comprise performing immunohistochemical analysis on the tissue sample. Embodiments as described herein can determine a subject's diagnosis, prognosis, or therapeutic approach. Embodiments as described herein can be used in combination with other methods known to the art to determine a subject's diagnosis, prognosis, or therapeutic approach. In some embodiments, a comparison can be conducted by assessing whether the peak(s) displayed in a mass spectrometric profile obtained from a sample subject overlays with the peak(s) displayed in a mass spectrometric profile obtained from a known, control, and/or reference sample.

An aspect of the present invention further provides a method of identifying non-Spitzoid malignant melanoma comprising subjecting a sample from a subject to mass spectrometry; obtaining a mass spectrometric profile from said sample; comparing said mass spectrometric profile to a profile obtained from a known normal, non-Spitzoid nevi and/or non-Spitzoid malignant melanoma sample; and identifying said lesion as a non-Spitzoid malignant melanoma if the mass spectrometric profile from the sample is similar to the mass spectrometric profile obtained from the known non-Spitzoid malignant melanoma. In some embodiments, a similarity is determined by assessing whether the peak(s) displayed in a mass spectrometric profile obtained from a sample subject overlays with the peak(s) displayed in a mass spectrometric profile obtained from a known, control, and/or reference sample. In embodiments, the similarity of the sample from the subject to a known profile, such as a known molecular profile, is determined using a statistical or machine learning algorithm. Non-limiting examples of the machine learning algorithm comprise a genetic algorithm, support vestor machine, or supervised neural network. In embodiments, the sample comprises a skin lesion sample, such as those with melanocytic components, stromal components, or a combination thereof. In other embodiments, the sample comprises any desired bodily tissue, non-limiting examples of which comprise blood, serum, cerebrospinal fluid, urine, sweat, saliva, skin, skin punches, or solid tissue biopsies. In embodiments, the mass spectrometric profile comprises one or more peaks at about m/z 1955, about m/z 1199, about m/z 1184, about m/z 1412, or about m/z 2216. In other embodiments, the mass spectrometric profile comprises one or more peaks at about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9. In embodiments, the mass spectrometric profile is also known as the molecular profile. In embodiments, the mass spectrometric profile comprises one molecule or a plurality of molecules. Non-limiting examples of types of molecules represented in the mass spectrometric profile comprise proteins, peptides, lipid, metabolites, nucleic acids or a combination thereof. In embodiments, the methods as described herein can further comprise the step of administering to the subject an effective amount of an anti-cancer agent. Non-limiting examples of such agents comprise chemotherapy, immunotherapy, toxin therapy, radiotherapy, or a combination thereof. In embodiments, non-limiting examples of mass spectrometry comprise secondary ion mass spectrometry, laser desorption mass spectrometry, matrix assisted laser desorption/ionization mass spectrometry, electrospray mass spectrometry, or desorption electrospray ionization. In embodiments, the methods as described herein can further comprise the step of obtaining a sample from said subject. For example, the subject can be a mammalian subject, for example, a human subject, such as one at risk of non-Spitzoid melanoma. In some embodiments, the mammal can be a canine, feline, or equine. In this example, a tissue sample can be obtained from the subject, and tested for biomarkers of melanoma using methods as described herein. The tissue can be obtained using methods known in the art. In embodiments, methods as described herein can further comprise the step of performing a mass spectrometric analysis of a known non-Spitz nevi, a known non-Spitzoid malignant melanoma lesion, or a combination thereof. For example, the known non-Spitzoid nevi or the known non-Spitzoid malignant melanoma lesion can be obtained from the subject whose sample tissue is being tested using embodiments and methods as described herein. In embodiments, the methods as described herein can further comprise performing histologic analysis on the tissue sample. Further, embodiments as described herein can also comprise performing immunohistochemical analysis on the tissue sample. Embodiments as described herein can determine a subject's diagnosis, prognosis, or therapeutic approach. Embodiments as described herein can be used in combination with other methods known to the art to determine a subject's diagnosis, prognosis, or therapeutic approach.

An aspect of the invention is directed to methods for identifying a non-Spitzoid melanoma. In one embodiment, the method comprises subjecting a tissue sample to mass spectrometry, wherein a sample mass spectrometric profile is produced; identifying the tissue as non-Spitzoid melanoma if the sample mass spectrometric profile comprises one or more peaks at about m/z 1955, about m/z 1199, about m/z 1184, about m/z 1412, or about m/z 2216, or one or more peaks at about the m/z listed in FIG. 6 or FIG. 7; and administering a therapeutically effective amount of an anti-cancer agent to the subject. In some embodiments, the mass spectrometric profile in FIG. 6 comprises one or more peaks at about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9. In embodiments, the mass spectrometric profile comprises a plurality of molecules. Non-limiting examples of types of molecules represented in the mass spectrometric profile comprise proteins, peptides, lipid, metabolites, nucleic acids or a combination thereof. Embodiments can further comprise the step of obtaining the tissue sample from a subject. In embodiments, the tissue sample comprises a skin lesion sample, such as those with melanocytic components, stromal components, or a combination thereof. In other embodiments, the sample comprises a sample of any desired bodily tissue, non-limiting examples of which comprise blood, serum, cerebrospinal fluid, urine, sweat, saliva, skin, skin punches, or solid tissue biopsies. Embodiments can further comprise the step of comparing the mass spectrometric profile obtained from the tissue sample to a mass spectrometric profile obtained from at least one control sample. For example, the control sample can be obtained from the subject itself. In another embodiment, the control sample can be obtained from a different subject. In embodiments, the control sample comprises a non-Spitz nevi tissue sample, a normal tissue sample, or both. In embodiments, the methods as described herein can further comprise the step of administering to the subject an effective amount of an anti-cancer agent. Non-limiting examples of such agents comprise chemotherapy, immunotherapy, toxin therapy, radiotherapy, or a combination thereof. In embodiments, non-limiting examples of mass spectrometry comprise secondary ion mass spectrometry, laser desorption mass spectrometry, matrix assisted laser desorption/ionization mass spectrometry, electrospray mass spectrometry, or desorption electrospray ionization.

An aspect of the invention is directed to methods of screening for the presence of a molecular signature in a subject at risk for non-Spitz melanoma. In one embodiment, the method comprises measuring at least one biomarker of non-Spitzoid melanoma in a tissue sample, wherein the biomarker comprises one or more peaks from a mass spectrometric profile at about m/z 1955, about m/z 1199, about m/z 1184, about m/z 1412, or about m/z 2216; comparing the non-Spitzoid melanoma biomarker profile to that of a profile obtained from at least one control sample; and treating the subject. In embodiments, the mass spectrometric profile further comprises one or more peaks at about m/z 1955, about m/z 1199, about m/z 1184, about m/z 1412, or about m/z 2216. In other embodiments, the mass spectrometric profile comprises one or more peaks at about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9. In other embodiments, the mass spectrometric profile comprises one or more peaks at about those as indicated in FIG. 6 or FIG. 7. Embodiments can further comprise the step of obtaining the tissue sample from a subject. In embodiments, the tissue sample comprises a skin lesion sample, such as those with melanocytic components, stromal components, or a combination thereof. In other embodiments, the sample comprises a sample of any desired bodily tissue, non-limiting examples of which comprise blood, serum, cerebrospinal fluid, urine, sweat, saliva, skin, skin punches, or solid tissue biopsies. In embodiments, the presence of at least one biomarker, the amount of at least one biomarker, or a combination thereof is measured. In embodiments, mass spectrometry is used to measure the biomarker. In embodiments, non-limiting examples of mass spectrometry comprise secondary ion mass spectrometry, laser desorption mass spectrometry, matrix assisted laser desorption/ionization mass spectrometry, electrospray mass spectrometry, or desorption electrospray ionization. In embodiments, the control sample comprises normal tissue, non-Spitz nevi, or both. In embodiments, the control sample can be obtained from the subject. In other embodiments, the control sample can be obtained from a different subject. In some embodiments, a comparison can be conducted by assessing whether the peak(s) displayed in a mass spectrometric profile obtained from a sample subject overlays with the peak(s) displayed in a mass spectrometric profile obtained from a known, control, and/or reference sample.

An aspect of the invention provides for diagnostic kits of molecular biomarkers for identifying a tissue as non-Spitz melanoma. In one embodiment, the kit comprises a means for detecting and/or a means for measuring, one or a combination of peaks from a mass spectrometric profile at about m/z 1955, about m/z 1199, about m/z 1184, about m/z 1412, or about m/z 2216, wherein the one or more peaks represent a molecular signature that is indicative of a non-Spitz melanoma. In embodiments, the molecular signature comprises one or more peaks at about m/z 1955, about m/z 1199, about m/z 1184, about m/z 1412, or about m/z 2216. In other embodiments, the mass spectrometric profile comprises one or more peaks at about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9. In other embodiments, the mass spectrometric profile comprises one or more peaks at about those as indicated in FIG. 6 or FIG. 7. In embodiments, the molecular signature comprises molecules such as proteins, peptides, lipid, metabolites, nucleic acids or a combination thereof. In embodiments, the molecular signature can comprise a protein or proteins selected from the group consisting of Actin, Histones, IgG, Glyceraldehyde-3-phosphate dehydrogenase, Vimentin, L-lactate dehydrogenase, Protein S100, Collagen, Filamin-A, Prelamin, HLA class I histocompatibility antigen, Cofilin-1, Tubulin, Heat shock protein, Serum amyloid, Endoplasmin, Keratin, Plectin, 14-3-3 protein epsilon, Synaptic vesicle membrane protein VAT-1, Elongation factor 1-alpha 1, Talin-1, Heterogeneous nuclear ribonucleoproteins, and Tenascin.

An aspect of the invention is directed to a method of identifying non-Spitzoid malignant melanoma. In one embodiment, the method comprises subjecting a skin lesion sample to mass spectrometry; obtaining a mass spectrometric profile from said sample, wherein the mass spectrometric profile comprises one or more peaks at about m/z 1955, about m/z 1199, about m/z 1184, about m/z 1412, or about m/z 2216; comparing said mass spectrometric profile to a profile obtained from a known normal, non-Spitz nevi and/or non-Spitzoid malignant melanoma sample; identifying said lesion as a non-Spitzoid malignant melanoma if the mass spectrometric profile from the sample is similar to the mass spectrometric profile obtained from the known non-Spitzoid malignant melanoma; and administering to the subject an effective amount of an anti-cancer agent. In embodiments, the similarity of the sample from the subject to a known profile, such as a known molecular profile, is determined using a statistical or machine learning algorithm. Non-limiting examples of the machine learning algorithm comprise a genetic algorithm, support vestor machine, or supervised neural network. In some embodiments, a similarity is determined by assessing whether the peak(s) displayed in a mass spectrometric profile obtained from a sample subject overlays with the peak(s) displayed in a mass spectrometric profile obtained from a known, control, and/or reference sample. In embodiments, the sample comprises a skin lesion sample, such as those with melanocytic components, stromal components, or a combination thereof. In other embodiments, the sample comprises any desired bodily tissue, non-limiting examples of which comprise blood, serum, cerebrospinal fluid, urine, sweat, saliva, skin, skin punches, or solid tissue biopsies. In embodiments, the mass spectrometric profile further comprises one or more peaks at about m/z 1955, about m/z 1199, about m/z 1184, about m/z 1412, or about m/z 2216. In other embodiments, the mass spectrometric profile comprises one or more peaks at about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9. In embodiments, the mass spectrometric profile is also known as the molecular profile. In embodiments, the mass spectrometric profile comprises one molecule or a plurality of molecules. Non-limiting examples of types of molecules represented in the mass spectrometric profile comprise proteins, peptides, lipid, metabolites, nucleic acids or a combination thereof. In embodiments, the methods as described herein can further comprise the step of administering to the subject an effective amount of an anti-cancer agent. Non-limiting examples of such agents comprise chemotherapy, immunotherapy, toxin therapy, radiotherapy, or a combination thereof. In embodiments, non-limiting examples of mass spectrometry comprise secondary ion mass spectrometry, laser desorption mass spectrometry, matrix assisted laser desorption/ionization mass spectrometry, electrospray mass spectrometry, or desorption electrospray ionization. In embodiments, the methods as described herein can further comprise the step of obtaining a sample from said subject. For example, the subject can be a mammalian subject, for example, a human subject, such as one at risk of non-Spitzoid melanoma. In some embodiments, the mammal can be a canine, feline, or equine. In this example, a tissue sample can be obtained from the subject, and tested for biomarkers of melanoma using methods as described herein. The tissue can be obtained using methods known in the art. In embodiments, methods as described herein can further comprise the step of performing a mass spectrometric analysis of a known non-Spitz nevi, a known non-Spitzoid malignant melanoma lesion, or a combination thereof. For example, the known non-Spitzoid nevi or the known non-Spitzoid malignant melanoma lesion can be obtained from the subject whose sample tissue is being tested using embodiments and methods as described herein. In embodiments, the methods as described herein can further comprise performing histologic analysis on the tissue sample. Further, embodiments as described herein can also comprise performing immunohistochemical analysis on the tissue sample. Embodiments as described herein can determine a subject's diagnosis, prognosis, or therapeutic approach. Embodiments as described herein can be used in combination with other methods known to the art to determine a subject's diagnosis, prognosis, or therapeutic approach.

An aspect of the invention is directed to methods of differentiating benign nevi from melanoma. In one embodiment, the method comprises subjecting a sample from a subject to mass spectrometry; obtaining a mass spectrometric profile from said sample; comparing said sample mass spectrometric profile to a profile obtained from a known normal nevus, an melanoma sample, or both, wherein the mass spectrometric profile comprises peaks at about m/z 1955, about m/z 1199, about m/z 1184, about m/z 1412, or about m/z 2216; and identifying said lesion as a benign nevus or melanoma based on the comparison of said sample mass spectrometric profile peaks and said known mass spectrometric profile peaks. In embodiments, the similarity of the sample from the subject to a known profile, such as a known molecular profile, is determined using a statistical or machine learning algorithm. Non-limiting examples of the machine learning algorithm comprise a genetic algorithm, support vestor machine, or supervised neural network. In some embodiments, a comparison can be conducted by assessing whether the peak(s) displayed in a mass spectrometric profile obtained from a sample subject overlays with the peak(s) displayed in a mass spectrometric profile obtained from a known, control, and/or reference sample. In embodiments, the mass spectrometric profile further comprises one or more peaks at about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9. In other embodiments, the mass spectrometric profile comprises one or more peaks at about those as indicated in FIG. 6 or FIG. 7. In other embodiments, the sample comprises any desired bodily tissue, non-limiting examples of which comprise blood, serum, cerebrospinal fluid, urine, sweat, saliva, skin, skin punches, or solid tissue biopsies. In embodiments, the mass spectrometric profile is also known as the molecular profile. In embodiments, the mass spectrometric profile comprises one molecule or a plurality of molecules. Non-limiting examples of types of molecules represented in the mass spectrometric profile comprise proteins, peptides, lipid, metabolites, nucleic acids or a combination thereof. In embodiments, the methods as described herein can further comprise the step of administering to the subject an effective amount of an anti-cancer agent. Non-limiting examples of such agents comprise chemotherapy, immunotherapy, toxin therapy, radiotherapy, or a combination thereof. In embodiments, non-limiting examples of mass spectrometry comprise secondary ion mass spectrometry, laser desorption mass spectrometry, matrix assisted laser desorption/ionization mass spectrometry, electrospray mass spectrometry, or desorption electrospray ionization. In embodiments, the methods as described herein can further comprise the step of obtaining a sample from said subject. For example, the subject can be a mammalian subject, for example, a human subject, such as one at risk of non-Spitzoid melanoma. In some embodiments, the mammal can be a canine, feline, or equine. In this example, a tissue sample can be obtained from the subject, and tested for biomarkers of melanoma using methods as described herein. The tissue can be obtained using methods known in the art. In embodiments, methods as described herein can further comprise the step of performing a mass spectrometric analysis of a known non-Spitz nevi, a known non-Spitzoid malignant melanoma lesion, or a combination thereof. For example, the known non-Spitzoid nevi or the known non-Spitzoid malignant melanoma lesion can be obtained from the subject whose sample tissue is being tested using embodiments and methods as described herein. In embodiments, the methods as described herein can further comprise performing histologic analysis on the tissue sample. Further, embodiments as described herein can also comprise performing immunohistochemical analysis on the tissue sample. Embodiments as described herein can determine a subject's diagnosis, prognosis, or therapeutic approach. Embodiments as described herein can be used in combination with other methods known to the art to determine a subject's diagnosis, prognosis, or therapeutic approach.

An aspect of the invention is directed to methods of identifying melanoma. In one embodiment, the method comprises subjecting a sample from a subject to mass spectrometry; obtaining a mass spectrometric profile from said sample; comparing said mass spectrometric profile to a profile obtained from a known normal, non-Spitzoid nevi and/or non-Spitzoid malignant melanoma sample, wherein the mass spectrometric profile comprises peaks at about m/z 1955, about m/z 1199, about m/z 1184, about m/z 1412, or about m/z 2216; and identifying said lesion as a non-Spitzoid malignant melanoma if the mass spectrometric profile from the sample is similar to the mass spectrometric profile obtained from the known non-Spitzoid malignant melanoma. In embodiments, the similarity of the sample from the subject to a known profile, such as a known molecular profile, is determined using a statistical or machine learning algorithm. Non-limiting examples of the machine learning algorithm comprise a genetic algorithm, support vestor machine, or supervised neural network. In some embodiments, a similarity is determined by assessing whether the peak(s) displayed in a mass spectrometric profile obtained from a sample subject overlays with the peak(s) displayed in a mass spectrometric profile obtained from a known, control, and/or reference sample. In embodiments, the sample comprises a skin lesion sample, such as those with melanocytic components, stromal components, or a combination thereof. In other embodiments, the sample comprises any desired bodily tissue, non-limiting examples of which comprise blood, serum, cerebrospinal fluid, urine, sweat, saliva, skin, skin punches, or solid tissue biopsies. In embodiments, the mass spectrometric profile further comprises one or more peaks at about m/z 1955, about m/z 1199, about m/z 1184, about m/z 1412, or about m/z 2216. In other embodiments, the mass spectrometric profile comprises one or more peaks at about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9. In embodiments, the mass spectrometric profile is also known as the molecular profile. In embodiments, the mass spectrometric profile comprises one molecule or a plurality of molecules. Non-limiting examples of types of molecules represented in the mass spectrometric profile comprise proteins, peptides, lipid, metabolites, nucleic acids or a combination thereof. In embodiments, the methods as described herein can further comprise the step of administering to the subject an effective amount of an anti-cancer agent. Non-limiting examples of such agents comprise chemotherapy, immunotherapy, toxin therapy, radiotherapy, or a combination thereof. In embodiments, non-limiting examples of mass spectrometry comprise secondary ion mass spectrometry, laser desorption mass spectrometry, matrix assisted laser desorption/ionization mass spectrometry, electrospray mass spectrometry, or desorption electrospray ionization. In embodiments, the methods as described herein can further comprise the step of obtaining a sample from said subject. For example, the subject can be a mammalian subject, for example, a human subject, such as one at risk of non-Spitzoid melanoma. In some embodiments, the mammal can be a canine, feline, or equine. In this example, a tissue sample can be obtained from the subject, and tested for biomarkers of melanoma using methods as described herein. The tissue can be obtained using methods known in the art. In embodiments, methods as described herein can further comprise the step of performing a mass spectrometric analysis of a known non-Spitz nevi, a known non-Spitzoid malignant melanoma lesion, or a combination thereof. For example, the known non-Spitzoid nevi or the known non-Spitzoid malignant melanoma lesion can be obtained from the subject whose sample tissue is being tested using embodiments and methods as described herein. In embodiments, the methods as described herein can further comprise performing histologic analysis on the tissue sample. Further, embodiments as described herein can also comprise performing immunohistochemical analysis on the tissue sample. Embodiments as described herein can determine a subject's diagnosis, prognosis, or therapeutic approach. Embodiments as described herein can be used in combination with other methods known to the art to determine a subject's diagnosis, prognosis, or therapeutic approach.

In embodiments, the subject can be a mammal. In some embodiments, the mammal can be a canine, feline, or equine.

Other objects and advantages of this invention will become readily apparent from the ensuing description.

BRIEF DESCRIPTION OF THE FIGURES

FIG. 6 shows the 25 peaks used in the SVM classifier. The mass spectrometric profile shows peaks at about those indicated in the figure.
FIG. 7 shows the peaks used in the SVM classifier. The mass spectrometric profile shows peaks at about those indicated in the figure.

DETAILED DESCRIPTION OF THE INVENTION

Abbreviations and Definitions

Figure 1:
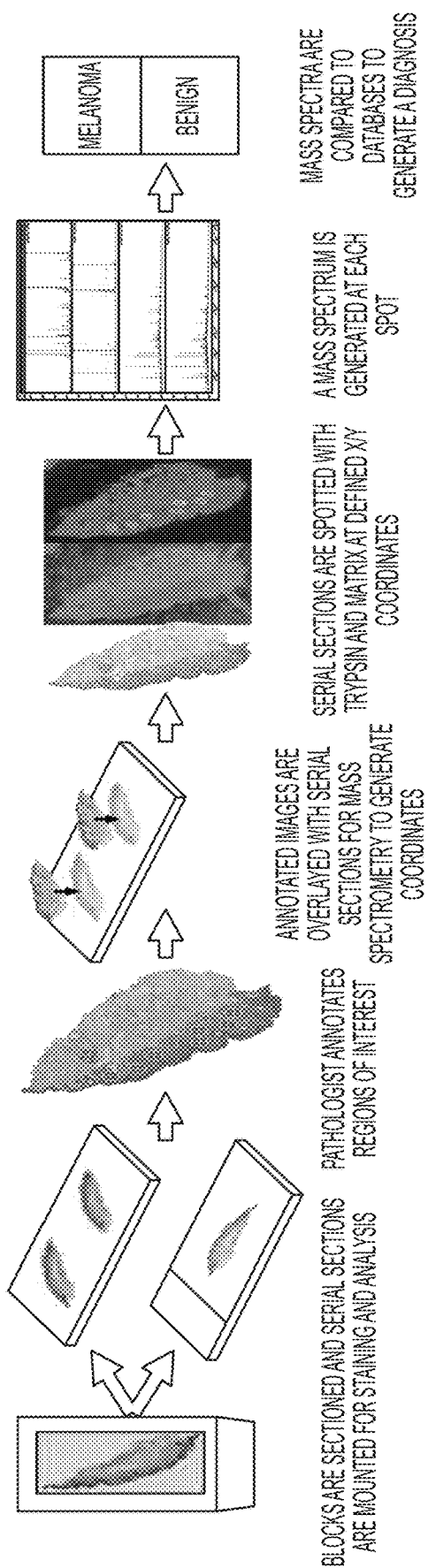
FIG. 1 shows histology-directed mass spectrometry.
Figure 2:
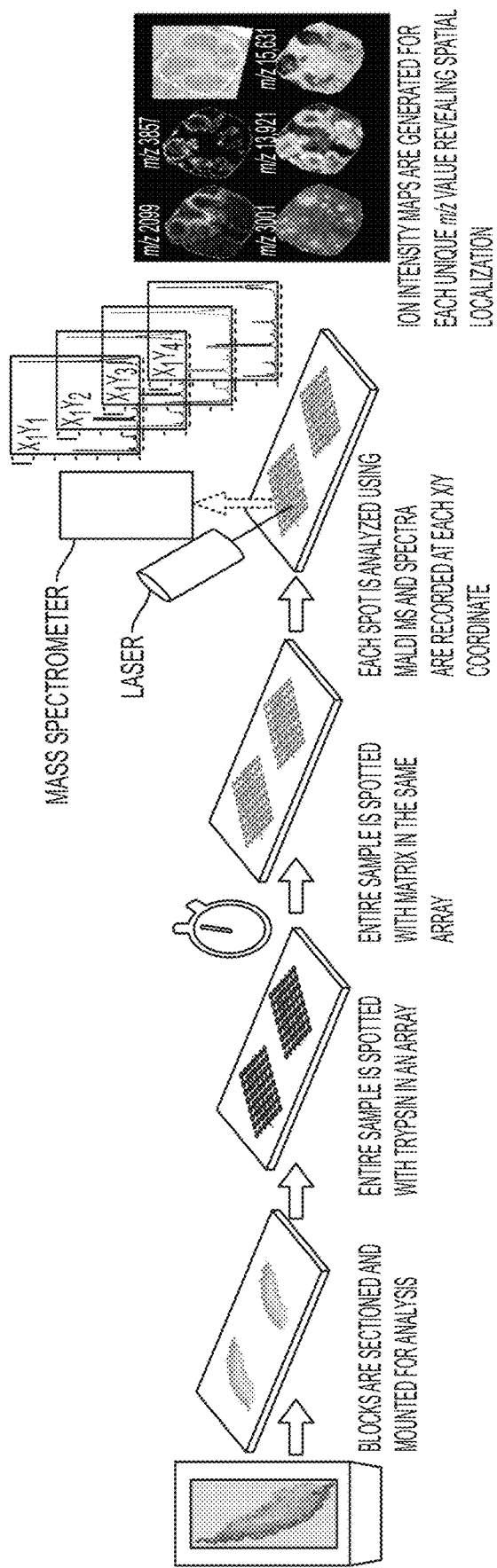
FIG. 2 shows imaging mass spectrometry.
Figure 3:
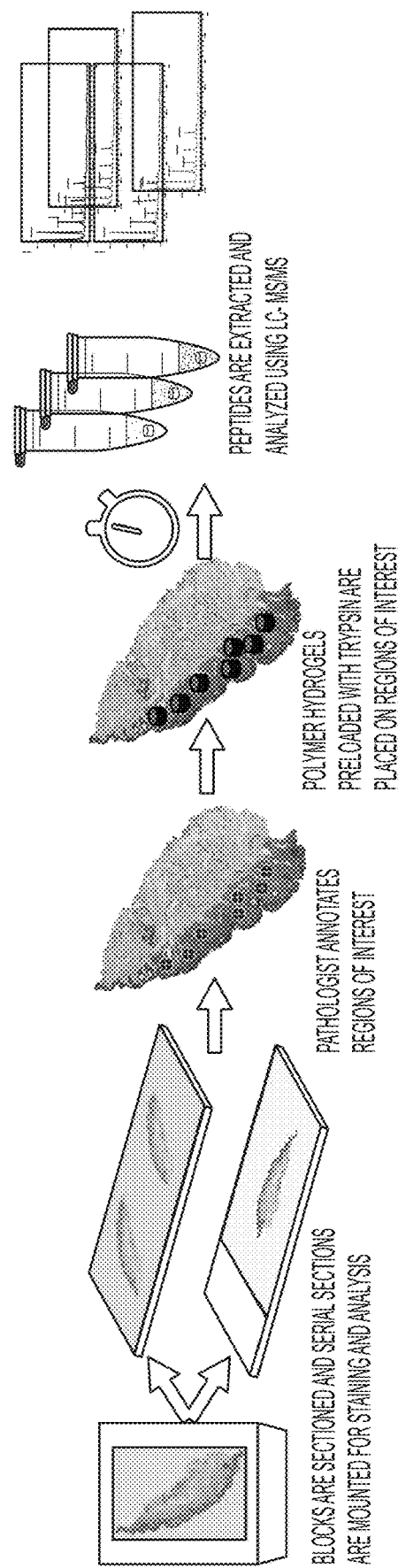
FIG. 3 shows hydrogel-based spatially targeted proteins.
Figure 4:
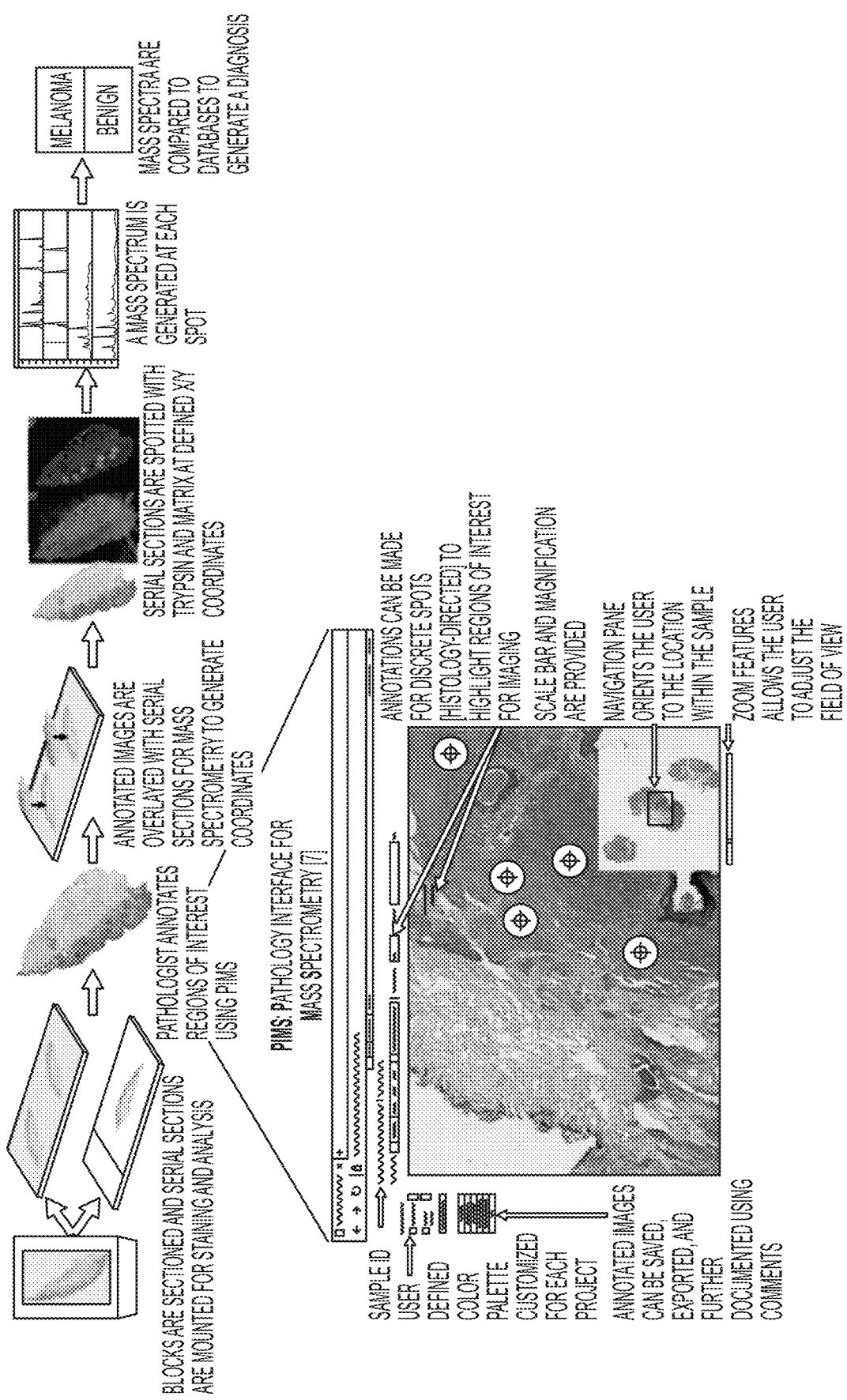
FIG. 4 shows histology-directed mass spectrometry.
Figure 5:
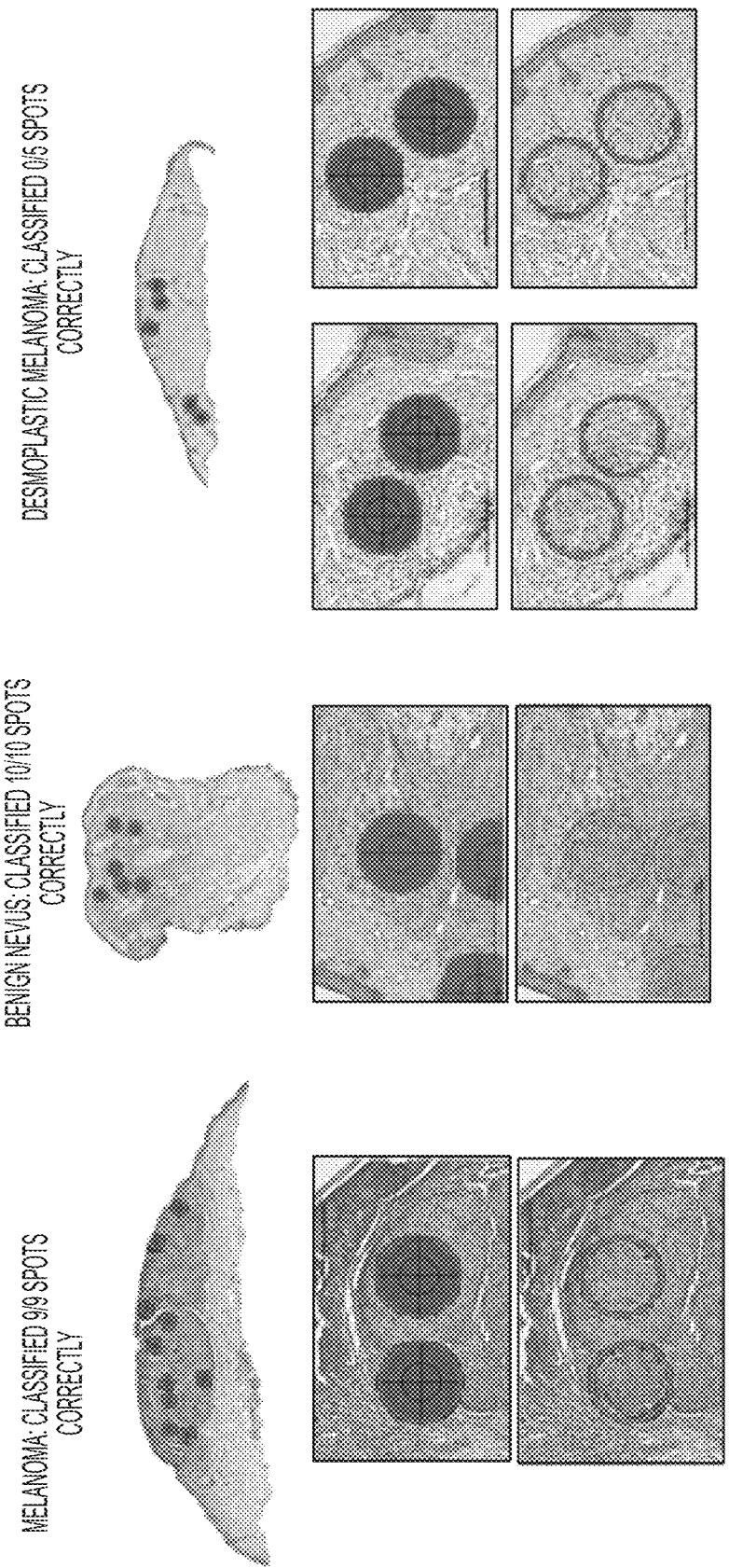
FIG. 5 shows case studies.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Melanoma

Melanoma is a malignant tumor of melanocytes. Melanocytes produce the dark pigment, melanin, which is responsible for the color of skin. These cells predominantly occur in skin, but are also found in other parts of the body, including the bowel and the eye (see uveal melanoma).

Melanoma can originate in any part of the body that contains melanocytes. Melanoma is less common than other skin cancers. However, it is much more dangerous if it is not found early. It causes the majority (75%) of deaths related to skin cancer. Worldwide, doctors diagnose about 160,000 new cases of melanoma yearly. It is more common in women than in men. In women, the most common site is the legs and melanomas in men are most common on the back. It is particularly common among Caucasians, especially northwestern Europeans living in sunny climates. There are high rates of incidence in Oceania, Northern America, Europe, southern Africa, and Latin America, with a paradoxical decrease in southern Italy and Sicily. This geographic pattern reflects the primary cause, ultraviolet light (UV) exposure crossed with the amount of skin pigmentation in the population.

According to a WHO report, about 48,000 melanoma related deaths occur worldwide per year. The treatment includes surgical removal of the tumor. If melanoma is found early, while it is still small and thin, and if it is completely removed, then the chance of cure is high. The likelihood of the melanoma coming back or spreading depends on how deeply it has gone into the layers of the skin. For melanomas that come back or spread, treatments include chemo- and immunotherapy, or radiation therapy.

Non-Spitzoid Nevi

According to the invention, Non-Spitzoid Nevi can be, for example, any skin lesion that does not exhibit the histological characteristics normally characterized as Spitzoid (for example, see Ferrara et al., "Spitz Nevus, Spitz Tumor, and Spitzoid Melanoma: A Comprehensive Clinicopathologic Overview," Dermatol Clin. 2013 October; 31(4):589-98, which is incorporated by reference in its entirety).

Non-Spitzoid Melanoma

According to the invention, Non-Spitzoid Melanoma can be any melanoma specimen that does not exhibit the histological characteristics normally characterized as Spitzoid (for example, see Ferrara et al., "Spitz Nevus, Spitz Tumor, and Spitzoid Melanoma: A Comprehensive Clinicopathologic Overview," Dermatol Clin. 2013 October; 31(4):589-98, which is incorporated by reference in its entirety).

Differentiating Non-Spitzoid Nevus from Non-Spitzoid Malignant Melanoma

An aspect of the invention is directed towards differentiating a non-Spitzoid nevus from non-Spitzoid malignant melanoma. "Differentiate" can refer to distinguishing between different disease states, for example between non-Spitzoid nevi and non-Spitzoid malignant melanoma. Detect, discriminate, discern, differentiate, and identify, for example, can be used interchangeably in the context of the invention as described herein.

In an embodiment, a sample, such as a sample of skin, is isolated or obtained from a subject and is subjected to mass spectrometry to provide a mass spectrometric profile. The mass spectrometric profile of the sample can then be compared to a mass spectrometric profile of a known normal, non-Spitz nevus, a known non-Spitzoid malignant melanoma, or both, so as to identify the sample lesion as a non-Spitz nevus or non-Spitzoid malignant melanoma.

The methods described herein typically involve isolating or obtaining a biological sample from the subject, such as a subject with a skin lesion. As used herein, the phrase "obtaining a skin sample" or "isolating a sample from a subject", for example, can refer to any process for directly or indirectly acquiring a biological sample from a subject. For example, a biological sample may be obtained (e.g., at a point-of-care facility, e.g., a physician's office, a hospital, laboratory facility) by procuring a tissue sample (such as a skin biopsy) from a subject. Alternatively, a biological sample may be obtained by receiving the biological sample (e.g., at a laboratory facility) from one or more persons who procured the sample directly from the subject. The biological sample may be, for example, a tissue (e.g., skin) or cell (e.g., epidermal cell) of a subject.

The term "skin" can refer to a tissue comprising a sheet of cells, one or several layers thick, organized above a basal lamina. In an embodiment, the skin is mammalian skin, such as that of a human. The term "sample" or "skin sample" can refer to any preparation derived from skin of a subject.

The epidermis of the human skin comprises several distinct layers of skin tissue, the deepest layer of which is the stratum basalis layer. The stratum basalis layer consists of columnar cells. The overlying layer is the stratum spinosum, which consists of polyhedral cells. Cells pushed up from the stratum spinosum are flattened and synthesize keratohyalin granules to form the stratum granulosum layer. As these cells move outward, they lose their nuclei, and the keratohyalin granules fuse and mingle with tonofibrils. This forms a clear layer called the stratum lucidum, which consists of closely packed cells. As the cells move up from the stratum lucidum, they become compressed into many layers of opaque squamae. These cells are all flattened remnants of cells that have become completely filled with keratin and have lost all other internal structure, including nuclei. These squamae constitute the outer layer of the epidermis, the stratum corneum. At the bottom of the stratum corneum, the cells are closely compacted and adhere to each other strongly, but higher in the stratum they become loosely packed, and eventually flake away at the surface.

In embodiments, the skin sample can comprise epidermal cells, such as an epidermis skin sample. The epidermis consists predominantly of keratinocytes (>90%), which differentiate from the basal layer, moving outward through various layers having decreasing levels of cellular organization, to become the cornified cells of the stratum corneum layer. Renewal of the epidermis occurs every 20-30 days in normal skin. Non-limiting examples of other epidermal cell types comprise melanocytes, Langerhans cells, and Merkel cells.

In embodiments, samples can be taken from a mole, or from another type of suspicious lesion (i.e. lesion suspected of being melanoma). Such lesions can reside in cosmetically problematical body parts, such as the face, the breast, the head, an arm or a leg. The samples are taken of the skin surface of the suspicious lesion using methods that are within the ability of those skilled in the art.

A "skin lesion" is a change in the color or texture in an area of skin. "Skin lesions suspected of being melanoma" are skin lesions with characteristics of malignant melanoma, which are well known to dermatologists and oncologists. Such lesions are sometimes raised and can have a color that is different from the color of normal skin of an individual (e.g. brown, black, red, or bluish). Lesions suspected of being melanoma sometimes include a mixture of colors, are often asymmetrical, can change in appearance over time, and may bleed. A skin lesion suspected of being melanoma may be a mole or nevus. Melanoma lesions are usually, but not always, larger than 6 mm in diameter. Melanoma includes superficial spreading melanoma, nodular melanoma, acral lentiginous melanoma, and lentigo-maligna melanoma. Melanoma can occur on skin that has been overexposed to the sun. Therefore, in one embodiment the skin sample is taken from an area of skin that has been overexposed to the sun.

The term "subject" or "patient" can refer to any organism to which aspects of the invention can be performed, e.g., for experimental, diagnostic, prophylactic, and/or therapeutic purposes. Typical subjects to which methods as described herein are performed comprise mammals, particularly primates, especially humans. For veterinary applications, a wide variety of subjects are suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals are suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

In an embodiment, the subject's mass spectrometric profile can be compared to that of a control sample, wherein a change in the mass spectrometric profile as compared to the control profile is associated with an increased likelihood of having and/or developing a non-Spitzoid melanoma. As used herein, "changed as compared to a control" sample or subject can refer to having a level of the analyte or diagnostic or therapeutic indicator (e.g., marker) to be detected at a level that is statistically different than a sample from a normal or abnormal state control sample. Determination of statistical significance is within the ability of those skilled in the art, e.g., the number of standard deviations from the mean that constitute a positive or negative result.

In an embodiment, a sample, such as a sample of skin, is isolated or obtained from a subject and is subjected to mass spectrometry to provide a mass spectrometric profile. The mass spectrometric profile of the sample can then be compared to a threshold value which is associated with an increased likelihood of having and/or developing a non-Spitzoid melanoma. The "threshold value" can refer to a value derived from a plurality of biological samples, such as donor skin samples.

Aspects of the invention are directed towards diagnosing or identifying a subject as having a non-Spitzoid melanoma. The term "diagnosing" can refer to classifying a melanoma as a non-Spitzoid melanoma, determining a severity of a non-Spitzoid melanoma melanoma, monitoring the progression of a non-Spitzoid melanoma, forecasting an outcome of a non-Spitzoid melanoma and/or prospects of recovery. The subject can be a healthy subject (e.g., human) undergoing a routine well-being checkup. Alternatively, the subject can be at risk of having a non-Spitzoid melanoma (e.g., a genetically predisposed subject, a subject with medical and/or family history of cancer, a subject who has been exposed to carcinogens, occupational hazard, environmental hazard] and/or a subject who exhibits suspicious clinical signs of melanoma (e.g., a change in the appearance of a mole).

Protein-Based Detection—Mass Spectrometry

By exploiting the intrinsic properties of mass and charge, mass spectrometry (MS) can be resolved and confidently identified a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can generate mass spectrometry profiles that are useful for characterizing skin cancers described herein. Mass spectrometry can also be used to look for the levels of the proteins selected from the group consisting of Actin, Histones, IgG, Glyceraldehyde-3-phosphate dehydrogenase, Vimentin, L-lactate dehydrogenase, Protein S100, Collagen, Filamin-A, Prelamin, HLA class I histocompatibility antigen, Cofilin-1, Tubulin, Heat shock protein, Serum amyloid, Endoplasmin, Keratin, Plectin, 14-3-3 protein epsilon, Synaptic vesicle membrane protein VAT-1, Elongation factor 1-alpha 1, Talin-1, Heterogeneous nuclear ribonucleoproteins, and Tenascin.

Electrospray Ionisation

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 µL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer is delivered to tip through an internal passage from a suitable source (such as from a chromatograph or directly from a sample solution via a liquid flow controller). By applying pressure to the sample in the capillary, the liquid leaves the capillary tip as small highly electrically charged droplets and further undergoes desolvation and breakdown to form single or multicharged gas phase ions in the form of an ion beam. The ions are then collected by the grounded (or negatively charged) interface plate and led through an orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258, which are incorporated herein by reference in their entireties.

Electrospray Ionisation Tandem Mass Spectrometry (ESI/MS/MS)

In ESI tandem mass spectrometry (ESI/MS/MS), one can simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000).

Secondary Ion Mass Spectrometry (SIMS)

Secondary ion mass spectrometry, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analyzed by the mass spectrometer in this method.

LD-MS and LDLPMS

Laser desorption mass spectrometry (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectrometry). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and the separation of fragments is due to different size causing different velocity. Each ion mass will thus have a different flight-time to the detector.

One can either form positive ions or negative ions for analysis. Positive ions are made from regular direct photoionization, but negative ion formation requires a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

MALDI-TOF-MS

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms in order to characterize endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a useful quantitative tool. MALDI-TOF-MS also allows non-volatile and thermally labile molecules to be analyzed with relative ease. Without being bound by theory, MALDI-TOF-MS can be useful for quantitative analysis in clinical settings, for toxicological screenings, as well as for environmental analysis. In addition, the application of MALDI-TOF-MS to the quantification of peptides and proteins is also useful. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which can contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al, 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multi-component quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

Immunohistochemistry

Antibodies can be used in conjunction with both fresh-frozen and/or formalin-fixed, paraffin-embedded tissue blocks prepared for study by immunohistochemistry (IHC). The method of preparing tissue blocks from these specimens has been successfully used in previous IHC studies of various prognostic factors, and/or is well known to those of skill in the art (Brown et al., 1990; Abbondanzo et al., 1999; Allred et al., 1990).

The present invention can also employ immunohistochemistry. This approach uses antibodies to detect and quantify antigens in intact tissue samples. Thin sections of tissue specimens are collected onto microscope slides. Samples that have been formalin-fixed and paraffin embedded must be subjected to deparaffinization and antigen retrieval protocols prior to incubation with an antibody against the target protein of interest. Deparaffinization is accomplished by incubating the slides in xylene to remove the paraffin followed by graded ethanol and water to rehydrate the sections. Antigen retrieval is carried out through incubating the sections in buffer such as tris or citrate with heat which may be introduced via a pressure cooker or a microwave. Sections can then be stained with antibodies using a direct or indirect method.

The direct method is a one-step staining method and involves a labeled antibody (e.g. FITC-conjugated antiserum) reacting directly with the antigen in tissue sections. While this technique utilizes only one antibody and therefore is simple and rapid, the sensitivity is lower due to little signal amplification, such as with indirect methods, and is less commonly used than indirect methods.

The indirect method involves an unlabeled primary antibody (first layer) that binds to the target antigen in the tissue and a labeled secondary antibody (second layer) that reacts with the primary antibody. As mentioned above, the secondary antibody must be raised against the IgG of the animal species in which the primary antibody has been raised. This method is more sensitive than direct detection strategies because of signal amplification due to the binding of several secondary antibodies to each primary antibody if the secondary antibody is conjugated to the fluorescent or enzyme reporter.

Mass Spectrometry Target Proteins

As discussed above, the present invention provides a protein-based classification of non-Spitz-like skin lesions. This classification is based on the identification of peaks for at least five peptides, the expression of which correlates with the various disease states. Using information derived from these five targets, one can differentiate non-Spitz nevi from non-Spitzoid malignant melanoma. In some embodiments, the classification can be further based on the identification of the peptides corresponding to the peaks for those listed in FIG. 6.

Mass Spectrometry Profile

In one embodiment, the invention examines mass spectrometry profiles of proteins from various regions of a skin lesion sample. The sample contains both melanocytic and stromal components, and one can examine either or both of these regions. The term "mass spectrometry profile" can refer to one or more proteins or a group of peptides from a sample isolated from a subject wherein the presence and the concentration of proteins or peptides, taken individually or together, is indicative/predictive of a certain condition, such as a non-Spitzoid melanoma.

In embodiments, the mass spectrometric profile comprises one or more peaks at about m/z 1955, about m/z 1199, about m/z 1184, about m/z 1412, or about m/z 2216. In other embodiments, the mass spectrometric profile comprises one or more peaks at about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9.

The classification model as described herein can be based on a peptide signature comprising any one the 25 mass spectrometric profile peaks listed in FIG. 6. The classification model as described herein can be based on a peptide signature comprising any one the 25 mass spectrometric profile peaks listed in FIG. 7. The top 5 highest weighted peaks used in the classification comprise about m/z 1955, about m/z 1199, about m/z 1184, about m/z 1412, or about m/z 2216.

With regarding to the melanocytic elements of the lesion, the invention identifies peptide peaks at a combination of about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9 as providing relevant information on the nature of the lesion.

When examining stromal components of the lesion, peptide peaks at about m/z 1954.9, about m/z 1199.0, about m/z 1184.9, about m/z 1411.8, about m/z 2216.3, about m/z 1791.7, about m/z 914.6, about m/z 2636.5, about m/z 1429.1, about m/z 1629.8, about m/z 3017.6, about m/z 1491.9, about m/z 734.4, about m/z 1132.7, about m/z 1985.1, about m/z 1488.0, about m/z 872.4, about m/z 1167.8, about m/z 1194.8, about m/z 1120.6, about m/z 1127.6, about m/z 1243.8, about m/z 2105.3, about m/z 1495.9, or about m/z 1466.9 are found to be relevant in distinguishing non-Spitz nevi from malignant melanoma.

In some embodiments, the peptide signature of the skin lesion can comprise at least 1, 2, 3, 4, 5, 6, 7, 8, 9, 10, 11, or 12 peaks from a mass spectrometric profile as listed in FIG. 6 or FIG. 7.

Classification Model

Spectral classification is achieved using the ClinProTools statistics package supplied by Bruker Daltonics. Spectra are organized and grouped according to the patient sample from which they originate. All spectra belonging to the same diagnosis are loaded into the software as a class with 2 or more classes being loaded for one analysis. All spectra are subjected to preprocessing which includes baseline subtraction, noise level estimation, and normalization to total ion current. Peak boundaries for integration and analysis are manually determined by selection of the monoisotopic peak. The peak data are then used to create a classification model using a genetic algorithm. In this approach, a set of peaks are chosen and evaluated for their ability to classify spectra into their correct diagnosis. This set of peaks is then crossed with another set of peaks, similar to genetic reproduction and the offspring evaluated for their classification ability. Those sets that perform better than the parents are further crossed with other sets to determine the most optimal set of peaks while those that perform worse, are discarded. This crossing and evaluation are carried out over 50 generations to determine the best optimized set of peaks for diagnostic classification. The maximum number of peaks to be used is set to 15, but the software determines the optimal number to include in the model.

Once a model has been optimized, it is evaluated using a leave-20%-out crossvalidation approach. A subset of 20% of the data is randomly selected to be left out and the remaining 80% are used to build the classification model. The model is then applied to the 20% that were originally left out and the accuracy of the classification determined. This is carried out over 10 iterations with a different random 20% left out each time.

Once an optimized classification model has been established, it can be applied to new data in one of two ways, either in a validation mode or a classification mode. In the validation mode, data are organized and identified as to the group to which they belong. The software then classifies the data and evaluates the accuracy of the classification reporting percentages of spectra correctly classified. In the classification mode, the researcher and the software are blinded as to the diagnoses of the sample from which the data originated. The software classifies the data into the group that it best matches and reports a list of classification results for each spectrum. Someone with knowledge of the clinical diagnosis of the samples must then evaluate the classification results as compared to the known diagnosis.

Protein Targets

Embodiments can comprise measuring at least one biomarker or protein target of non-Spitzoid melanoma, non-Spitzoid nevus, or a combination thereof so as to identify non-Spitzoid melanoma or non-Spitzoid nevus. The term "marker" or "biomarker" can refer to a protein that is differentially expressed in a tissue sample, such as a non-Spitzoid melanoma sample, as compared to a normal sample.

In embodiments of the invention, protein targets useful in the identification and treatment of Non-Spitzoid Nevi and/or Non-Spitzoid Melanoma include, but are not limited to, Actin, Histones, IgG, Glyceraldehyde-3-phosphate dehydrogenase, Vimentin, L-lactate dehydrogenase, Protein 5100, Collagen, Filamin-A, Prelamin, HLA class I histocompatibility antigen, Cofilin-1, Tubulin, Heat shock protein, Serum amyloid, Endoplasmin, Keratin, Plectin, 14-3-3 protein epsilon, Synaptic vesicle membrane protein VAT-1, Elongation factor 1-alpha 1, Talin-1, Heterogeneous nuclear ribonucleoproteins, and Tenascin.

Non-Spitzoid Malignant Melanoma Therapies

Based on the stage of the cancer and other factors, treatment options for non-Spitzoid melanoma comprise surgery, immunotherapy, targeted therapy, chemotherapy, or radiation therapy.

Generally, early stage cancer can be treated with surgery alone, but more advanced cancers often require other treatments, including multiple treatments such as adjuvant therapy.

Non-limiting examples of immunotherapies comprise interferon, interleukin-2, pembrolizumab, nivolumab, ipilimumab.

Non-limiting examples of targeted therapies comprise vemurafenib, dabrafenib, trametrinib, and codimetinib, imatinib, and nilotinib.

Non-limiting examples of chemotherapies comprise dacarbazine and temozolomide.

Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Supplementary active ingredients also can be incorporated into the compositions.

Administration of these compositions according to the present invention will be via any common route so long as the target tissue is available via that route. This includes intradermal, subcutaneous, intramuscular, intraperitoneal or intravenous injection. In particular, intratumoral routes and sites local and regional to tumors are contemplated. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy administration by a syringe is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration the polypeptides of the present invention may be incorporated with excipients that may include water, binders, abrasives, flavoring agents, foaming agents, and humectants.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Kits

Embodiments can further comprise a diagnostic kit of molecular biomarkers, for example for identifying a tissue as non-Spitz melanoma. In one embodiment, the kit comprises (a) a container that contains a tools for obtaining and/or storing a tissue sample from a subject, and optionally (b) informational material. The informational material can be descriptive, instructional, marketing or other material that relates to the methods described herein and/or the use of the agents for therapeutic or diagnostic benefit.

The informational material of the kits is not limited in its form. In one embodiment, the informational material can include information about mass spectrometry, non-Spitzoid melanoma and/or non-Spitzoid nevus, a list of protein targets and/or biomarkers, molecular weight of the protein targets, information about therapeutic agents (such as concentration, date of expiration, batch or production site information), and so forth. In one embodiment, the informational material relates to methods of differentiating non-Spitzoid nevus from non-Spitzoid malignant melanoma. The information can be provided in a variety of formats, include printed text, computer readable material, video recording, or audio recording, or an information that provides a link or address to substantive material.

If desired, the composition in the kit can include a therapeutic agent and, optionally, other ingredients, such as a solvent or buffer, a stabilizer, or a preservative. The therapeutic can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight. The kit optionally includes a device suitable for administration of the composition, e.g., a syringe or other suitable delivery device. The device can be provided preloaded with one or both of the agents or can be empty, but suitable for loading.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Current Practices in Anatomic Pathology

The practice of anatomic pathology relies heavily on visual inspection of cell morphology by trained physicians, specializing in specific disease pathologies. In spite of the rigorous training systems that have been devised to raise and maintain the standard of care, there are disease states for which the current practice cannot provide a definitive diagnosis. For example, early detection of melanoma remains an important factor in increasing survival rates of patients with this malignancy. For early melanoma cases (<1 mm in thickness), the survival is above 90% at 10 years. However, early diagnosis of melanoma is often difficult because many melanocytic lesions show conflicting histopathologic criteria, intermediate between benign and malignant, and are frequently interpreted differently by dermatopathologists (1, 2).

The addition of specific molecular measurements to aid physicians in the interpretation of disease states in anatomic pathology significantly improves the standard of care and will lead to better patient outcomes. Currently, this molecular information is most often provided by staining the biopsy section for single proteins or examining genes expression changes. However, this approach in moving forward to achieve improved diagnoses has major disadvantages as we go forward to achieve much improved diagnoses through the use of multiplex tests where many proteins are to be measured in a 'signature' of disease. Multiple staining of a biopsy section is very difficult if not practically impossible and, further, with respect to the it would entail significant time and expense to develop these probe and antibodies.

The Need for New Technology

Nowhere is a molecular description of disease needed more than in the histology/pathology laboratory where biopsy assessments are performed that have life changing implications. Unfortunately, visual inspection by an individual physician introduces subjectivity into the diagnosis, and in many cases significant disagreement can occur even among experts. In one study, diagnostic discrepancies ranged from 15% to 25% of cases (3). An expert panel review of 1069 melanocytic lesions considered 14% (22/158) of the cases initially classified as invasive melanoma, as benign, and 16.6% (85/513) of the cases originally classified as benign, malignant (4).

We are well into a molecular age in medicine, one promising the capability to fully describe disease at the molecular level. Seminal advances in the effective diagnosis and treatment of disease is most often preceded by innovations in the technology used to probe cells and tissue biopsies. Genomics has initiated a revolution in the way we characterize disease; however, many genomic analyses require the use of laser capture microdissection. This method is capable of providing the regiospecificity needed to target specific cell types in tissue, but is costly given the sensitivity and labor/time required for the analysis. Furthermore, genome measurements only describe the potential or probability for disease to occur. The disease phenotype, represented in the proteome and metabolome of the cell, accurately represents the biochemical state of the disease at the time of biopsy, which is much more useful for accurate diagnosis and treatment.

Solution

Imaging mass spectrometry (IMS) combines the spatial information of microscopy with the unparalleled molecular specificity and sensitivity of mass spectrometry to create molecular image maps of molecules in tissues. Briefly, the technology employs the process of laser ablation of specific cells on the target tissue followed by ionization and analysis of the ablated molecules. Each signal, among thousands in the mass spectrum from a single ablation spot, can be plotted by mass-to-charge (essentially molecular weight) monitored at specific locations on the tissue, giving rise to a molecular map of individual molecules that can be correlated with the tissue morphology. Many hundreds of discrete molecular maps can be generated from a single analysis of the tissue biopsy section. This technology has distinct advantages over other current technologies used for the analysis of tissues because it provides: (1) a label-free (no antibodies or probes needed) approach to the detection of thousands of possible disease biomarkers, (2) cell-type specific molecular analysis without time-consuming microdissection or other lengthy tissue preparation, and (3) a means for objective disease classification based only on molecular profiles of proteins, metabolites, and lipids.

The laser-based MS platform is not expected to be disease specific. The same instrument can be used for the diagnosis of any number of disease conditions as long as the diagnostic signature is known from discovery experiments. The analysis train, from sample preparation, digital imaging, MS analysis, and subsequent bioinformatics analysis remains constant for all diagnostic tests developed using this technology.

As described herein, imaging mass spectrometry will be used in a histology-directed mode, wherein discrete spots on the tissue section are ablated as directed by a pathologist. In this specific use case, mass spectra are the basis for an objective classification of each discrete tissue area according to the specific suite of molecules expressed in the cells contained in these areas. Specifically, Matrix-assisted laser desorption/ionization (MALDI) will be used to enable the accurate analysis of molecular measurements that indicate specific disease conditions.

The technology is highly reliable and robust in terms of the accuracy and reproducibility of molecular measurements from tissue biopsies or other clinical samples. Mass spectrometry instrumentation used in this diagnostic application can be quite simple to operate and has extremely high reliability with 'uptime' being >95% or more. The necessary workflow and protocols developed by the founders of Frontier have been shown to be robust from repeated tests and validation processes (see Phase I/II preliminary data).

Proteomics has proven utility in the clinical lab for impacting patient outcomes. The use of proteomic signatures measured by mass spectrometry has recently been validated and accepted for use in the clinical laboratory. Examples include FDA approved MALDI-TOF instruments and protocols for the identification of microorganisms from Bruker Daltonics (Bremen, Germany) and bioMérieux (Marcy l'Etoile, France), and diagnostic pathology using LC-MS/MS for protein analyses for Alzheimer's disease as performed by The Mayo Clinic (5).
Key Technology Objectives.

The innovation as described herein is the development of a more accurate, faster diagnostic test for the classification of atypical melanocytic lesions based upon a multiplex protein signature. A molecular signature using MALDI mass spectrometry has been devised for the direct analysis of patient biopsies that differentiates benign and malignant melanocytic lesions with higher overall classification accuracy, sensitivity, and specificity than commercially available diagnostic technologies.

Though there is a substantial body of literature describing the use of MALDI MS technology in research (6), with clear technological advantages for the analysis of tissue sections, it has not yet been applied for the diagnosis of disease in a clinical setting. The primary technical hurdles for commercializing this as a clinical test are threefold: First, the technology must be validated as more accurate for definitive identification of lesions, while remaining cost effective for clinicians to use. Second, institutional hurdles remain because of the newness of the basic technology for biopsy examination in the pathology laboratory. Finally, the absence of expertise for this technology may slow its adoption in the current clinical environment. Accordingly, the inventors have demonstrated that this this technology can be used to provide clinically actionable results that would influence patient care if available to the treating physician (7).

In preliminary research, a proprietary molecular signature has been developed using MALDI (matrix-assisted laser desorption ionization) mass spectrometry for the analysis of patient biopsies that employs a multiplex signature of 5 key proteins that differentiate these two lesions (7, 8). The test is performed on formalin-fixed paraffin embedded tissue biopsies, the standard for tissue preservation in pathology laboratories. Since the initial publication, we have analyzed over 250 biopsies from different patients and have either confirmed the initial diagnosis to be correct, or particularly in the cases of atypical lesions where the specific diagnosis was unknown at the time of biopsy, demonstrated that MALDI MS can accurately diagnose the disease. Since many of these biopsies were obtained from tissue banks with some samples dating back 10 to 15 years prior to our analysis, we have the advantage of patient follow-up and outcome to validate our results. To date, all of the identifications made using the inventor's technology have been correct, validated by patient outcomes. In particular, over 40 atypical biopsies that were categorized as probable melanomas were identified by our technology to be benign lesions and these patients are alive and well today with no evidence of disease some 2-14 years later. Sample preparation for mass spectrometry analysis of typically 10 biopsies on a glass microscope slide takes less than 30 minutes and the laser ablation mass spectrometric analysis itself takes less than 1 minute per biopsy.

The invention described herein will validate, develop, and commercialize the use of MALDI MS for the classification of difficult-to-diagnose melanocytic lesions. There are often lesions that are difficult to assess and diagnose using conventional histology. Thus, the use of the inventions described herein are useful to diagnose melanoma when the histology is inconclusive.

Research results will be validated through analysis of a 100 patient cohort of Spitzoid lesions, and will provide proof-of-concept ms to develop and validate the use of MALDI MS for the classification of difficult to diagnose melanocytic lesions. Proof-of-concept for a faster, more accurate analytical methodology that is scalable and economically viable for application in a clinical laboratory will be established. These objectives will be accomplished through the development of a high-throughput tissue digestion procedure and automation of the data processing and analysis procedures for disease classification. Optimum performance of these developments will be confirmed through the analysis of a 100 patient cohort of Spitzoid lesions.

The platform will also be validated for the diagnosis of atypical melanocytic lesions and on a larger patient cohort, and will optimize the bioinformatics platform to meet the requirements for use in the clinical lab. The sample preparation methods will be optimized and standardized to achieve reproducible results, develop quality control and assurance procedures to control for inter- and intra-day variation of results, and optimize pathology interface software developed in house for commercial release. Further, a validated and fully documented standard operating procedure for melanoma diagnosis ready for commercialization by a CLIA-approved clinical laboratory will be developed. These method and software optimizations will be designed and documented to meet Clinical Laboratory Improvement Amendments (CLIA) standards for commercial diagnostic assays.

Successful completion of the research as described herein will demonstrate that mass spectrometry-based diagnosis of melanocytic lesions has an overall classification accuracy, sensitivity, and specificity that significantly exceeds the capabilities of the current tests. Further, a validated and fully documented standard operating procedure for melanoma diagnosis ready for commercialization by a CLIA-approved clinical laboratory will be developed. This melanocytic lesion test represents an important milestone for the development and application of MALDI MS in pathology. Diagnosis of melanoma is recognized to be an extremely difficult problem in pathology; therefore, successful commercialization of this test is expected to will fund drive the adoption of the development of our technology for in other diseases. As the technology is adopted to solve difficult problems, it is anticipated that this platform technology will be established as a new standard that permits unbiased stratification of diseased populations, redefining our understanding of disease on a molecular level.

Potential Societal, Educational, and Scientific Benefits

In the United States, melanoma is the 5th and 6th most common cancer in men and women, respectively (9). With an estimated 76,250 new cases in 2012, its incidence rates since 2004 have been increasing at 3% per year in both white men and women, a faster rise than known for any other major cancer in fair-skinned White populations (9). Since failure to diagnose melanoma poses both medical and legal risks, there exists a significant incentive for over-diagnosis and classifying ambiguous lesions as melanoma (10). Considering the increasingly large number of biopsies (>2M biopsies per year to rule out melanoma), this represents a significant problem that is likely to negatively impact patient care and result in substantial costs to the healthcare system. If diagnosed early, removal of melanoma costs approximately $1,800 per patient, with an excellent survival. However, treatment costs increase substantially as the melanoma advances, rising to well in excess of $150,000 per patient at the later stages of the disease (11). More importantly, the long-term health of the patient is compromised if chemotherapy is administered to patients that are incorrectly diagnosed with melanoma.

Described herein is the development of a diagnostic test for the classification of atypical melanocytic lesions based upon a multiplex protein signature. A molecular signature using MALDI mass spectrometry for the direct analysis of patient biopsies that differentiates benign and malignant melanocytic lesions will be developed. The successful development of this technology will provide anatomical pathologists with the tools to probe tissues directly without the limitations and expense of antibodies. For clinical research, the potential for discovery is maximized using MALDI MS since target specific reagents (such as antibodies) are not required. In short, the direct molecular mapping in disease is the solution to the need for greater molecular specificity and multiplexing and so is now critical in molecular pathology and will continue to be in the coming years to keep up with the fast moving molecular age. This technology represents a paradigm shift in the field of anatomic pathology that provides the pathologist with new highly specific tools to carry out their vital work (12). This innovative approach to tissue pathology will be applied to numerous disease areas, and will open up the opportunity to make significant improvements to patient care For the first time, anatomical pathologists will have the tools to probe tissues directly without the limitations and expense of antibodies. For clinical research, the potential for discovery is maximized using MALDI MS since target specific reagents (such as antibodies) are not required. In short, the direct molecular mapping in disease is the solution to the need for greater molecular specificity and multiplexing and so is now critical in molecular pathology and will continue to be in the coming years to keep up with the fast moving molecular age. This technology represents a paradigm shift in the field of anatomic pathology that provides the pathologist with new highly specific tools to carry out their vital work (12). This innovative approach to tissue pathology will be applied to numerous disease areas, and will open up the opportunity to make significant improvements to patient care.

An initial diagnostic test that differentiates benign nevi and melanomas utilizing laser-based mass spectrometry will be developed. Current pathology techniques based on cell and tissue morphology cannot clearly distinguish these lesions in a large number of cases and in such instances, the standard of care then dictates the treatment of the patient with chemotherapeutic agents. Uncertain diagnoses often leads to the classification of lesions as atypical, resulting in treatments that should ideally be reserved only for malignant disease due to the negative side effects and cost of administration. Well over half of atypical lesions are benign and so expensive drug treatments and future health risks due to therapy are unnecessary.

There are a number of demographic factors and variety of pressures that that will increase the need for advanced, integrated tools to support enable future pathology labs in the future. First, with an aging general population, along with an expected increase in the incidence of cancer and related screening programs, there will be a growing need for more pathology tests, leading to an increase in the number of tissue/tumor biopsy samples to be processed by existing pathology labs. Secondly, and concurrent with this expected increase in the testing load, there is expected to be a decrease in available pathologists. In the US alone, the number of actively practicing pathologists is expected to decrease from 18,000 in 2010 (about 5.7 per 100,000 population) to 14,000 in 2030 (about 3.7 per 100,000 population)—a 35% per capita decrease (13, 15). This anticipated decline is expected to place significant pressure on existing pathologists and pathology labs, creating a need to provide the remaining pathologists with new, more accurate, faster, and more cost effective new tools to maximize their productivity. Finally, many healthcare systems are expected to look for integrated diagnostics in order to reduce the total cost and increase the quality of healthcare. In Western Europe, a rigorous effort is underway to offer "connected care." Consequently, a major focus exists on digital pathology and is expected to generate demand for increasing the efficiency and accuracy in of the existing workflow of pathology labs (13).

Skin Cancer in the U.S.

In 2012, an estimated 76,250 new cases will be diagnosed (annual increase of 3% since 2004) (9). The number of biopsies performed in the US to rule out melanoma is 2 million per year. Of these, 25% cannot be definitively classified using routine histopathology (3). Based on these key assumptions, there were potentially 500,000 assays per year in 2012, growing to ca. 672,000 by the year 2022.

Next, the study will be expanded to include all melanocytic lesions that have conflicting diagnostic criteria. In a separate analysis, this expansion of scope increases the estimate to include 5% of melanoma diagnoses that cannot be definitively diagnosed using routine histopathology.

Histology

The gold standard for the diagnosis of melanoma remains histologic evaluation. Architectural and cytologic features of the biopsy are interpreted in the context of clinical information. Immunohistochemical markers such as MART-1, MiTF, HMB45, Ki67, p16 are currently used to help distinguish melanoma from nevi. However, they have to be used in the context of histologic examination; there is no tissue-based assay that successfully discriminates benign versus malignant melanocytic tumors or one that is used for prognostic classification (17).

Genomics

Techniques to classify melanocytic tumors based on changes in chromosomal copy number changes such as comparative genomic hybridization (CGH) and fluorescent in-situ hybridization (FISH) have received more attention in recent years (3, 18). CGH has been used in selected centers as a diagnostic tool for ambiguous melanocytic tumors and although it is useful in some circumstances, it is laborious and time-consuming. Tumor cells must be microdissected since a relatively pure tumor population is required and laser-capture microdissection may be necessary. The DNA then needs to be isolated and purified from the tumor sample, labeled with a fluorochrome, and hybridized. Additionally, the copy number change must be represented by at least 30% to 50% of the collected cells for it to be evident in the analysis. Hence, CGH may yield a false-negative result in melanoma arising with a nevus (19, 20) or in lesions with inflamed or fibrous stroma. Based on CGH findings, a more practical 4-probe FISH panel has been introduced to differentiate non-ambiguous melanocytic lesions with a sensitivity of 83-87% and a specificity of 95% in discriminating malignant versus benign (3). Problems such as tetraploidy—especially in benign Spitz type melanocytic proliferations—can introduce false positive results. In addition, the most current NeoGenomics data indicate that up to 25% of unequivocal melanomas are expected to show a normal FISH signal pattern. In subtypes such as desmoplastic melanoma, false negative rates will be up to 50% by FISH (21). As expected, FISH assays on histologically ambiguous lesions show lower sensitivity and specificity rates (43 and 80%, respectively) (22). Another study on ambiguous melanocytic tumors using clinical outcome as the final end-point measure compared FISH results with clinical behavior and reached an overall sensitivity of 60% and a specificity of 50% for later development of metastases (23).

Specific commercial diagnostic tests that address specific diagnostic problems in skin cancer include:

Immunostaining, FISH and CGH: as described herein

Melanoma Tumor Typing: Selected genetic mutations (e.g., BRAF, RAS, KIT, PTEN) are tested to determine the most effective therapy. This technique is applied to detect actionable mutations, (i.e., suitable to be used in targeted therapies.). However, mutation analysis does not provide information to apply to the differential diagnosis between benign and malignant melanocytic lesions.

Castle Biosciences, DecisionDx-Melanoma: A 31-gene panel designed to identify the Stage I and II patients whose tumor biology suggests they are at higher or lower risk of metastasis than their stage might indicate. Although this technique is useful for prognostic purposes, it does not provide information to apply to the differential diagnosis between benign and malignant melanocytic lesions.

NeoTYPE™ Melanoma Profile: This technique provides information on possible targets for therapy through sequencing of select exons of the genes listed. (e.g., BRAF, CTNNB1, EGFR, ERBB2, ERBB4, KIT, NRAS, PDGFRA and SMO. This technique provides information on possible targets for therapy), but it is not suitable for diagnostic purposes.

DermTech: sequencing of select exons of the genes listed. BRAF, CTNNB1, EGFR, ERBB2, ERBB4, KIT, NRAS, PDGFRA and SMO. DermTech: The company is developing novel gene classifiers and expression tests to provide objective biological information on dermatologic conditions. Uniquely, DermTech's assays can be used on samples collected non-invasively with an adhesive patch rather than a scalpel, but n. No tests are currently on the market.

Myriad Genetics, Inc., myPath™ Melanoma: 23-gene panel designed to distinguish melanoma from benign nevi. This test represents the most direct competition for the test that will be developed in the project; however, the results are preliminary and little is known about the commercial success of this test at the time of this grant submission. This This test is still under research development; in one study using several hundred samples, the results differentiated with high sensitivity and specificity malignant melanoma from benign skin lesions using traditional dermatopathology as a gold standard; however, this technique requires the homogenization and extraction of the DNA to be carried out. It is not amenable to histology-directed analysis on a few cells. As such, this assay will be influenced greatly by the dilution effect, leading to an increased frequency of false negative results.

Technological Advantage

1) Sensitivity

Histology-directed MALDI MS analysis can be performed on a minimal specimen (down to 100 50 µm areas on the biopsy), making it possible to analyze only selected diseased cells. This is an advantage since many diseases are known to be heterogeneous at the tissue level. Most approaches to molecular testing provide spatial information that can be correlated to tissue histology for a select, targeted small number of analytes, or the technique provides a more global view of the molecular events in the tissue at the expense of spatial information. In genomics, for example, many tests require homogenization and extraction of DNA from the whole tissue biopsy in order to provide enough material for testing (i.e., myPath Melanoma). This leads to significant dilution of the desirable DNA changes in the disease tissue into a background of normal cellular DNA. Thus, the detection of aberrant genomic information is less sensitive, limiting the application of the technology to only a portion of the collected specimens. Furthermore, this dilution effect limits the assays utility for early detection, a disease state in which only a minimal number of malignant cells exist in the sample. This limits the application of the test technology to late stage disease where the potential for effective intervention is diminished.

2) Speed

In order to correlate genetic markers with tissue histology, one of two approaches can be used. For global analyses, laser microdissection is typically used to collect specific cell types for analysis and to accumulate enough material to achieve the necessary sensitivity. This approach adds significant cost and expense due to the labor intensive nature of this technique. Alternatively, tissue based approaches utilized specific antibodies or probes to stain for targeted markers. The disadvantage of this approach is that one must develop those reagents and validate their use for a specific application.

One of the major advantages of the use of MALDI MS is that the analysis can be performed with significant increase in speed over existing technologies, particularly those requiring dissection of the cells of interest. Furthermore, the mass spectrometry approach does not require the use of tagging chemistry, instead the biological molecule is measured directly from the tissue in its native state. These types of efficiencies will enable the assay to be provided at a competitive price against other technologies while providing outstanding turnaround time, enabling application of the technology platform at the point of care.

This is in contrast to current methods where in order to correlate genetic markers with tissue histology, one of two approaches can be used. For global analyses, laser microdissection is typically used to collect specific cell types for analysis and to accumulate enough material to achieve the necessary sensitivity. This approach adds significant cost and expense due to the labor intensive nature of this technique. Alternatively, tissue based approaches utilized specific antibodies or probes to stain for targeted markers. The disadvantage of this approach is that one must develop those reagents and validate their use for a specific application.

The primary end-user of the melanoma diagnostic service are practicing dermatopathologists. Since the target application is difficult to diagnose melanocytic lesions, the pathologist is key in the identification of cases for which the test is warranted.

The melanoma test described herein can be a lab developed test and the service will be performed in a CLIA laboratory. This approach will not require FDA approval to commercialize the test; however, the test must be performed in accordance with CLIA laboratory standards.

REFERENCES CITED IN THIS EXAMPLE

1. Crowson, N., Magro, C., and Mihm, M. (2001) The Melanocytic Proliferations, Wiley-Liss, Inc, New York.
2. Massi, G., and Leboit, P. (2004) Histological Diagnosis of Nevi and Melanoma, Springer Verlag, Berlin.

3. Gerami, P., Jewell, S. S., Morrison, L. E., Blondin, B., Schulz, J., Ruffalo, T., Matushek, P. t., Legator, M., Jacobson, K., Dalton, S. R., Charzan, S., Kolaitis, N. A., Guitart, J., Lertsbarapa, T., Boone, S., LeBoit, P. E., and Bastian, B. C. (2009) Fluorescence in situ hybridization (FISH) as an ancillary diagnostic tool in the diagnosis of melanoma, Am J Surg Pathol 33, 1146-1156.
4. Veenhuizen, K. C., De Wit, P. E., Mooi, W. J., Scheffer, E., Verbeek, A. L., and Ruiter, D. J. (1997) Quality assessment by expert opinion in melanoma pathology: experience of the pathology panel of the Dutch Melanoma Working Party, J Pathol 182, 266-272.
5. Vrana, J. A., Gamez, J. D., Madden, B. J., Theis, J. D., Bergen, H. R., 3rd, and Dogan, A. (2009) Classification of amyloidosis by laser microdissection and mass spectrometry-based proteomic analysis in clinical biopsy specimens, Blood 114, 4957-4959.
6. Norris, J. L., and Caprioli, R. M. (2013) Analysis of tissue specimens by matrix-assisted laser desorption/ionization imaging mass spectrometry in biological and clinical research, Chem Rev 113, 2309-2342.
7. Lazova, R., Seeley, E. H., Keenan, M., Gueorguieva, R., and Caprioli, R. M. (2012) Imaging mass spectrometry—a new and promising method to differentiate Spitz nevi from Spitzoid malignant melanomas, Am J Dermatopathol 34, 82-90.
8. Morgan, T. M., Seeley, E. H., Fadare, O., Caprioli, R. M., and Clark, P. E. (2013) Imaging the clear cell renal cell carcinoma proteome, J Urol 189, 1097-1103.
9. (2012) Cancer Facts and Figures, The American Cancer Society.
10. Troxel, D. B., and Sabella, J. D. (1994) Problem areas in pathology practice. Uncovered by a review of malpractice claims, Am J Surg Pathol 18, 821-831.
11. Poole, C. (2014) The Cost of Melanoma: Early Detection Could Save Millions of Lives, Melanoma International Foundation.
12. Norris, J. L., and Caprioli, R. M. (2013) Imaging mass spectrometry: a new tool for pathology in a molecular age, Proteomics Clin Appl 7, 733-738.
13. (2013) Analysis of the Global Tissue Diagnostics Market., Frost & Sullivan.
14. (2009) U.S. Tissue Diagnostics Market., Frost & Sullivan.
15. Robboy, S. J., Weintraub, S., Horvath, A. E., Jensen, B. W., Alexander, C. B., Fody, E. P., Crawford, J. M., Clark, J. R., Cantor-Weinberg, J., Joshi, M. G., Cohen, M. B., Prystowsky, M. B., Bean, S. M., Gupta, S., Powell, S. Z., Speights, V. O., Jr., Gross, D. J., and Black-Schaffer, W. S. (2013) Pathologist workforce in the United States: I. Development of a predictive model to examine factors influencing supply, Archives of pathology & laboratory medicine 137, 1723-1732.
16. Taguchi, F., Solomon, B., Gregorc, V., Roder, H., Gray, R., Kasahara, K., Nishio, M., Brahmer, J., Spreafico, A., Ludovini, V., Massion, P. P., Dziadziuszko, R., Schiller, J., Grigorieva, J., Tsypin, M., Hunsucker, S. W., Caprioli, R., Duncan, M. W., Hirsch, F. R., Bunn, P. A., Jr., and Carbone, D. P. (2007) Mass spectrometry to classify non-small-cell lung cancer patients for clinical outcome after treatment with epidermal growth factor receptor tyrosine kinase inhibitors: a multicohort cross-institutional study, J Natl Cancer Inst 99, 838-846.
17. Sabel, M. S., Liu, Y., and Lubman, D. M. (2011) Proteomics in melanoma biomarker discovery: great potential, many obstacles, Int J Proteomics 2011, 181890.
18. Bastian, B. C., Olshen, A. B., LeBoit, P. E., and Pinkel, D. (2003) Classifying melanocytic tumors based on DNA copy number changes, Am J Pathol 163, 1765-1770.
19. Bauer, J., and Bastian, B. C. (2006) Distinguishing melanocytic nevi from melanoma by DNA copy number changes: comparative genomic hybridization as a research and diagnostic tool, Dermatol Ther 19, 40-49.
20. Gerami, P., and Zembowicz, A. (2011) Update on fluorescence in situ hybridization in melanoma: state of the art, Arch Pathol Lab Med 135, 830-837.
21. Gerami, P., Beilfuss, B., Haghighat, Z., Fang, Y., Jhanwar, S., and Busam, K. J. (2011) Fluorescence in situ hybridization as an ancillary method for the distinction of desmoplastic melanomas from sclerosing melanocytic nevi, J Cutan Pathol 38, 329-334.
22. Vergier, B., Prochazkova-Carlotti, M., de la Fouchardiere, A., Cerroni, L., Massi, D., De Giorgi, V., Bailly, C., Wesselmann, U., Karlseladze, A., Avril, M. F., Jouary, T., and Merlio, J. P. (2011) Fluorescence in situ hybridization, a diagnostic aid in ambiguous melanocytic tumors: European study of 113 cases, Mod Pathol 24, 613-623.
23. Gaiser, T., Kutzner, H., Palmedo, G., Siegelin, M. D., Wiesner, T., Bruckner, T., Hartschuh, W., Enk, A. H., and Becker, M. R. (2010) Classifying ambiguous melanocytic lesions with FISH and correlation with clinical long-term follow up, Mod Pathol 23, 413-419.

Example 2

Imaging Mass Spectrometry to Differentiate Benign Melanocytic Nevi from Melanoma Imaging Mass Spectrometry (IMS) is a new tool that can detect proteomic signatures. Imaging mass spectrometry (IMS) is a new tool that can provide proteomic information from specific cell types within formalin-fixed, paraffin-embedded tissues. IMS has been used to differentiate Spitzoid Melanoma from Spitz Nevi and to diagnosis other cancers including breast, prostate, renal and liver cancers. We sought to identify differences in proteomic information in non-Spitzoid Melanoma as compared to conventional melanocytic nevi. IMS analysis was performed on 30 non-Spitzoid Melanoma and 30 conventional melanocytic nevi. Proteomic differences between the two groups were detected.

Clinical Study Specimens

The specimens utilized in this project are from the archives of Pathology Associates of St. Thomas, Nashville, Tenn. and were obtained under an approved protocol (IRB ID #5596). A patient cohort of 67 biopsies was analyzed using IMS, consisting of 33 benign nevi and 34 invasive melanoma. The specimens were deidentified by Pathology Associates of St. Thomas and provided to co-investigators at the Vanderbilt University Mass Spectrometry Research Center for mass spectral analysis.

TABLE 1

Summary of the study cohort

| Lesion type | Number of cases | Average age | Gender |
| --- | --- | --- | --- |
| Benign nevi | 33 | 50.9 | Male (17), Female (16) |
| Melanoma | 34 | 62.4 | Male (19), Female (15) |

Methods

Sample Preparation: Specimens were prepared for analysis by mass spectrometry as previously described.[1,2] Serial sections of each tissue specimen were prepared and mounted onto conductive indium-tin-oxide coated glass microscope slides. One serial section was selected for staining and uploaded to a web-based image server. Each stained section was annotated to identify up to 10 regions of interest (300 µm diameter) where further molecular analysis was performed.

The annotated stained image was aligned with the unstained tissue section in order to transfer coordinates of the annotations to the unstained section. In situ digestion of the tissue was performed using the trypsin followed by the application of the MALDI matrix α-cyano-4-hydroxy-cinnamic acid.

Data acquisition: Mass spectra were acquired from each location using a Bruker Ultraflextreme III MALDI-TOF/TOF mass spectrometer. The instrument was operated in reflector mode, tuning for optimal signal in the range of m/z 600-4000.

Data Analysis: Statistical analyses of mass spectral profiles were performed using ClinProTools 2.2 (Bruker Daltonics). For this study, specimens were randomly assigned to a training set or validation set (Table 2). Spectral data was prepared for analysis by applying algorithms for baseline subtraction, noise reduction, and peaks were identified and peak intensities were computed to permit statistical analysis. A classification model that distinguishes benign nevi from invasive melanoma was built using a support vector machine algorithm applied to the training cohort. This model was validated using the specimens set aside in the Validation set. The methods for this approach have been described in a previous publication.

TABLE 2

Sample cohorts for training and validation

| Lesion type | Benign Nevi | Melanoma | Total |
| --- | --- | --- | --- |
| Training Set | 24 | 25 | 49 |
| Validation Set | 9 | 9 | 18 |

Results

The classification model was based on a peptide signature comprising 25 peaks. The top 5 highest weighted peaks used for classification and their relative weight are listed in Table 3.

TABLE 3

Top 5 weighted peaks used for spectral classification of Melanoma.

| m/z value | Relative weight in Classifier |
| --- | --- |
| 1954.9 | 1.11 |
| 1199.0 | 1.00 |
| 1184.9 | 0.91 |
| 1411.8 | 0.90 |
| 2216.3 | 0.89 |

The overall classification accuracy of the model within the training set specimens was 100% (49 of 49 patients classified correctly) (Table 4).

TABLE 4

Training Set Results

| Lesion type | Number of cases | Corrects diagnosis by MALDI MS | Classification Accuracy (%) |
| --- | --- | --- | --- |
| Benign nevi | 24 | 24 | 100 |
| Melanoma | 25 | 25 | 100 |

The classification model was applied to each individual spot in the Validation Set in order to confirm the validity of the model for the classification of unknown specimens. For confirmation, we required 60% or more of the spectra within each case match the clinical diagnosis. Table 5 shows the results of the classification of the validation set. The MALDI-based classifier for the diagnosis of melanoma was confirmed to have a sensitivity of 89% and specificity of 100%.

TABLE 5

Validation Set Results

| Lesion type | Number of cases | Correct diagnosis by MALDI MS | Classification Accuracy (%) |
| --- | --- | --- | --- |
| Benign nevi | 9 | 9 | 100 |
| Melanoma | 9 | 8 | 89 |

Further analysis of the of the data underlying these results reveal that the melanocytic lesion that did not classify correctly was a desmoplastic type melanoma, a melanoma subtype that was not adequately represented in the training set (n=1). Further, examination of the H&E section and the area of analysis reveal that the cellular composition was largely . . . . If this case were excluded from the analysis, the assay would have achieved 100% sensitivity for the classification of melanoma.

SUMMARY

Conclusions:
A patient cohort of 67 biopsies was analyzed using IMS, consisting of 33 benign melanocytic nevi and 34 invasive melanoma.
Spectral differences were determined using statistical analysis and machine learning.
Classification accuracy for each subgroup in the training set was 100%.
The MALDI-based classifier for the diagnosis of melanoma was confirmed using an independent validation set to have a sensitivity of 89% and specificity of 100% due to the incorrect classification of a single desmoplastic melanoma.
Histology-directed mass spectrometry was demonstrated to differentiate benign melanocytic nevi from invasive melanoma reliably.
Future Directions
Analysis of additional biopsies to build statistical power, extending the patient cohort for both testing and training sets.
Work is underway to identify the peptides used in the classification algorithm.
The differential expression of these peptides will be confirmed using traditional approaches, including immunostaining methods.

REFERENCES CITED IN THIS EXAMPLE

Nat Protoc. 2011 Oct. 13; 6(11):1695-709.
Am J Dermatopathol. 2012 February; 34(1):82-90.

Example 3

Introduction
Early and Accurate Detection of Melanoma

The most important factor to increase patient survival rates is early and accurate detection of melanoma. Early diagnosis is difficult because many melanocytic lesions present with conflicting histopathologic criteria, which can be interpreted differently by dermatopathologists [1]. Considering the ever increasing number of biopsies, this presents a serious problem likely to negatively impact patient care and result in significant costs to the healthcare system [2]. An objective, tissue-based assay to discriminate benign vs malignant melanocytic tumors would benefit patients and the healthcare system. Currently, there is no tissue-based proteomics assay to discriminate or to yield prognostic classification of these lesions [3].

MALDI Mass Spectrometry and Molecular Pathology

MALDI mass spectrometry presents the ability to analyze biomolecules from cells directly from tissue sections [4]. Recently, a similar workflow demonstrated the capability to accurately differentiate Spitz nevus from Spitzoid melanoma [5,6].

Methods
Clinical Study Specimens

The specimens utilized in this project are from the archives of Pathology Associates of St. Thomas, Nashville, Tenn. and were obtained under an approved protocol (IRB ID #5596). A patient cohort of 67 biopsies was analyzed using IMS, consisting of 33 benign nevi and 34 non-Spitzoid, invasive melanomas. Among the melanoma cases, Breslow depth ranged from 0.4-4.1 mm with an average of 1.42 mm. The specimens were de-identified by Pathology Associates of St. Thomas and provided to coinvestigators at the Vanderbilt University Mass Spectrometry Research Center for mass spectral analysis.

TABLE 6

Summary of Study Cohort

| Lesion Type | Number of Cases | Average Age (Range) | Gender |
|---|---|---|---|
| Benign nevi | 33 | 50.9 (13-80) | Male (17), Female (16) |
| Melanomas | 34 | 62.4 (23-92) | Male (19), Female (15) |

Histology-Directed Mass Spectrometry
Data Analysis

Statistical analyses of mass spectral profiles were performed using ClinProTools 2.2 (Bruker Daltonics). For this study, specimens were randomly assigned to a training set or validation set. Spectral data was prepared for analysis by applying algorithms for baseline subtraction and noise reduction. Peaks were identified and peak intensities were computed to permit statistical analysis. A classification model that distinguishes benign nevi from invasive melanomas was built using a support vector machine applied to the training set. This model was validated using the specimens set aside in the validation set. The methods for this approach have been described in detail in previous publications [5,6].

TABLE 7

Sample Cohorts for Training and Validation

| | Benign Nevi | Melanoma | Total |
|---|---|---|---|
| Training Set | 24 | 25 | 49 |
| Validation Set | 9 | 9 | 18 |

Building a Classification Algorithm

The classification model was based on a peptide signature comprising 25 peaks. The top 5 highest weighted peaks used in classification and their relative weights are listed below:

TABLE 8

Top 5 Weighted Peaks used for Spectral Classification of Melanoma

| m/z value | Relative weight in Classifier |
|---|---|
| 1954.9 | 1.11 |
| 1199.0 | 1.00 |
| 1184.9 | 0.91 |
| 1411.8 | 0.90 |
| 2216.3 | 0.89 |

The overall classification accuracy of the model within the training set specimens was 100% (49 of 49 patients classified correctly).

TABLE 9

Training Set Results

| Lesion Type | Number of Cases | Correct Diagnosis by MALDI MS | Classification Accuracy (%) |
|---|---|---|---|
| Benign nevi | 24 | 24 | 100 |
| Melanomas | 25 | 25 | 100 |

The classification model was applied to each individual spot in the validation set in order to confirm the validity of the model for the classification of unknown specimens. For confirmation, we required 60% or more of the spectra within each case match the clinical diagnosis. Table 5 shows the results of the classification of the validation set. The MALDI-based classifier for the diagnosis of melanoma was confirmed to have a sensitivity of 89% and specificity of 100%.

TABLE 10

Validation Set Results

| Lesion Type | Number of Cases | Correct Diagnosis by MALDI MS | Classification Accuracy (%) |
|---|---|---|---|
| Benign nevi | 9 | 9 | 100 |
| Melanomas | 9 | 8 | 89 |

Further analysis of the data underlying these results revealed that the melanocytic lesion that did not classify correctly was a desmoplastic type melanoma, a melanoma subtype that was not adequately represented in the training set (n=1). Examination of the H&E section revealed that the desmoplastic melanoma was hypocellular with a prominent desmoplastic stroma. If this case were excluded from the analysis, the assay would have achieved 100% sensitivity for the classification of melanoma.

Case Studies
  Melanoma: Classified 9/9 spots correctly
  Benign Nevus: Classified 10/10 spots correctly
  Desmoplasmic Melanoma: Classified 0/5 spots correctly Conclusions and Future Directions Histology-directed mass spectrometry workflows were shown to differentiate benign nevi from melanomas reliably. Future directions include the continuation of testing new biopsies to build statistical power by extending the patient cohort for both training and validation sets. Future directions also include the identification of the peptides used in the classification algorithm. The peptide changes and localization will be confirmed using traditional approaches, including immunostaining methods.

REFERENCES CITED IN THIS EXAMPLE

1. Massi, G., Leboit, P. (2004) Histological Diagnosis of Nevi and Melanoma, Springer Verlag, Berlin.
2. Poole, C. (2014) The Cost of Melanoma: Early Detection Could Save Millions of Lives, Melanoma International Foundation.
3. Sabel. M. S., Liu, Y., Lubman, D. M., (2011) Proteomics in Melanoma Biomarker Discovery: Great Potential, Many Obstacles, Int J Proteomics. 2011: 181890.
4. Norris, J. L., Caprioli, R. M., (2013) Imaging Mass Spectrometry: A New Tool for Pathology in a Molecular Age. Proteomics Clin. Appl. 7 (11-12):733-8.
5. Lazova, R., Seeley, E. H., Keenan, M., Guerorguieeva, R., Caprioli, R. M., (2012) Imaging Mass Spectrometry—a new and promising method to differentiate Spitz nevi from Spitzoid malignant melanomas. Am J Dermatopathol. 34 (1):82-90.
6. Lazova, R., et al. (2016) Imaging mass spectrometry assists in the classification of diagnostically challenging atypical Spitzoid neoplasms. J AmAcad Dermatol. pii: 50190-9622 (16): 30483-2.
7. Norris, J. L.; Tsui, T.; Gutierrez, D. B.; Caprioli, R. M. (2016) Pathology interface for the molecular analysis of tissue by mass spectrometry. J Pathol Inform. 2016 7:13.

Example 4

Overview of Analytical Process for Skin Classification
  1. Tissue biopsies are formalin-fixed and paraffin embedded
  2. Tissues are sectioned and are placed onto conductive glass slides
  3. Tissue sections are deparaffinized using xylenes and antigen retrieved using buffer and heat
  4. Serial sections are histologically stained and uploaded to an online interface
  5. Pathologists use the online web interface to annotate regions of interest
  6. Annotations are matched to the sections for analysis
  7. A robotic spotter is used to apply enzyme and matrix to the annotated regions
  8. A MALDI mass spectrometer is used to take measurement at each annotated region
  9. The mass spectra are compared to a database of spectra from patients with known outcomes.
  10. The spectra are assigned to a disease state based on mass spectral fingerprint matching Table 11: Confusion table and statistics on the test's ability to classify non-Spitzoid melanoma and benign lesions from patient samples with classifications in accordance with pathology highlighted in grey. The data was randomly split with class balance into a training (n=117 patient samples) and a test set (n=39 patient samples) and a cross-validated support vector machine model was used for classification.

TABLE 11

| Prediction | Reference | |
|---|---|---|
| | Benign | Melanoma |
| Benign | 18 | 1 |
| Melanoma | 1 | 19 |
| Accuracy: | 0.9487 | |
| Sensitivity: | 0.9474 | |
| Specificity: | 0.95 | |

Example 5

Melanoma Versus Benign Samples

The classification of each spot within a sample is performed independently. The accuracy was approximately 0.95 when using the criterion that a majority of spots dictate the classification of each patient.

TABLE 12

| Overview | | | |
|---|---|---|---|
| | n samples | n samples melanoma | n samples benign |
| Training set | 117 | 59 | 58 |
| Test set | 39 | 20 | 19 |
| Pre-processing | | | |

TIC
normalization
TopHat Baseline reduction
Savitzky-Golay smoothing
Spectral alignment to overall mean
Peak Picking, snr = 3
Peak Binning, 0.2 Da tolerance
Peak filtering, min occurrence in 10% of spectra
n of features = 846
Model Support Vector Machine with Linear Kernel
5 k-fold cross validation with 10 repeats per fold

TABLE 13

| sample_name | labeled_class | majority_by_sample | maj_percentage |
|---|---|---|---|
| 501_Bottom_Benign | Benign | Benign | 1 |
| 502_Top_Melanoma | Melanoma | Melanoma | 1 |
| 503_Top_Orange_melanoma | Melanoma | Benign | 0.666666667 |
| 504_top_green_Benign | Benign | Benign | 1 |
| 505_Top_Green_Benign | Benign | Benign | 1 |
| 506_Middle_Benign_poorcrystals | Benign | Benign | 1 |

TABLE 13-continued

| sample_name | labeled_class | majority_by_sample | maj_percentage |
|---|---|---|---|
| 506_Top_Melanoma | Melanoma | Melanoma | 1 |
| 507_Top_Melanoma | Melanoma | Melanoma | 1 |
| 508_Top_Benign | Benign | Benign | 1 |
| 509_Bottom_Melanoma | Melanoma | Melanoma | 1 |
| 510_Bottom_Melanoma | Melanoma | Melanoma | 1 |
| 511_Top_Melanoma | Melanoma | Melanoma | 1 |
| 512_bottom_melanoma | Melanoma | Melanoma | 1 |
| 512_Top_Benign | Benign | Benign | 0.9 |
| 513_bottom_melanoma_SuperficialSpreading | Melanoma | Melanoma | 0.9 |
| 513_Middle_Benign_Bad_crystals | Benign | Benign | 0.8 |
| 514_bottom_melanoma_some_poor_crystals | Melanoma | Melanoma | 1 |
| 514_Middle_benign | Benign | Benign | 0.714285714 |
| 515_Middle_Melanoma | Melanoma | Melanoma | 1 |
| 516_Middle_Melanoma | Melanoma | Melanoma | 1 |
| 517_Top_Melanoma | Melanoma | Melanoma | 1 |
| 518_Top_Benign | Benign | Benign | 0.888888889 |
| 519_Middle_Benign | Benign | Benign | 1 |
| 520_Middle_Benign_Poor_Crystals | Benign | Benign | 1 |
| 520_Top_Melanoma | Melanoma | Melanoma | 1 |
| 522_Bottom_Benign | Benign | Benign | 0.9 |
| 523_Bottom_Benign | Benign | Benign | 0.8 |
| 603_Bottom_Benign | Benign | Benign | 1 |
| 603_Middle_Melanoma | Melanoma | Melanoma | 1 |
| 605_Middle_Benign | Benign | Benign | 1 |
| 606_Bottom_Benign | Benign | Benign | 1 |
| 606_Middle_Benign | Benign | Benign | 0.947368421 |
| 608_Middle_Melanoma | Melanoma | Melanoma | 1 |
| 611_Middle_Melanoma | Melanoma | Melanoma | 1 |
| 612_Middle_Melanoma | Melanoma | Melanoma | 1 |
| 613_Bottom_Melanoma | Melanoma | Melanoma | 1 |
| 614_Middle_Benign | Benign | Benign | 1 |
| 619_Bottom_Melanoma | Melanoma | Melanoma | 1 |
| 619_Top_Benign | Benign | Benign | 0.888888889 |

TABLE 14

Benign vs Melanoma
Spectral Level
Confusion Matrix and Statistics

| | Reference | |
|---|---|---|
| Prediction | Benign | Melanoma |
| Benign | 159 | 3 |
| Melanoma | 16 | 192 |
| Accuracy: | 0.9486 | |
| 95% CI : | (0.921, 0.9688) | |
| No Information Rate: | 0.527 | |
| P-value [Acc > NIR]: | <2.2e-16 | |
| Kappa: | 0.8966 | |
| mcnemar's Test P-value: | 0.005905 | |
| sensitivity: | 0.9086 | |
| specificity: | 0.9846 | |
| Pos Pred value: | 0.9815 | |
| Neg Pred value: | 0.9231 | |
| Prevalence: | 0.473 | |
| Detection Rate: | 0.4297 | |
| Detection Prevalence: | 0.4378 | |
| Balanced Accuracy: | 0.9466 | |
| 'Positive' class: | Benign | |

TABLE 16

Benign vs Melanoma
Sample level - by majority
Confusion Matrix and Statistics

| | Reference | |
|---|---|---|
| Prediction | Benign | Melanoma |
| Benign | 18 | 1 |
| Melanoma | 1 | 19 |
| Accuracy: | 0.9487 | |
| 95% CI: | (0.8268, 0.9937) | |
| No Information Rate : | 0.5128 | |
| P-Value [Acc > NIR]: | 3.45E-09 | |
| Kappa: | 0.8974 | |
| Mcnemar's Test P-Value: | 1 | |
| Sensitivity: | 0.9474 | |
| Specificity: | 0.95 | |
| Pos Pred Value: | 0.9474 | |
| Neg Pred Value: | 0.95 | |
| Prevalence: | 0.4872 | |
| Detection Rate: | 0.4615 | |
| Detection Prevalence: | 0.4872 | |
| Balanced Accuracy: | 0.9487 | |
| 'Positive' class: | Benign | |

Example 6

A cohort of melanocytic lesions was used with known clinical outcomes to validate the overall classification accuracy for the detection of melanoma from FFPE skin biopsies. >95% classification accuracy for the validation set with >95% sensitivity and specificity. For example, results were obtained showing 98.3% Accuracy; 96.7% Sensitivity; and 100% Specificity.

Cohort Composition.

A total of 302 skin samples were processed in the Phase I cohort. The specimens were de-identified. Of the 302 skin samples, 142 were benign samples, composed of compound nevi, intradermal nevi, and blue nevi. Of the 160 melanocytic lesions, 78 represented superficial spreading, 29 lentigo maligna, and 53 other melanomas. Only superficial spreading and lentigo maligna, the two most common subtypes of melanoma, were used in the statistical analysis. A summary of the biopsies processed is provided in Table 17.

TABLE 17

Patient Cohort Data

| Pathology | No. of Cases | Male | Female | Age Range (years) | Age Avg. (years) | Breslow Range (mm) | Breslow Average (mm) |
|---|---|---|---|---|---|---|---|
| Melanoma-Superficial Spreading | 77 | 38 | 39 | 21-89 | 56.6 | 0.2-3.3 | 1.03 |
| Melanoma-Lentigo Maligna | 32 | 19 | 13 | 48-93 | 69.8 | 0.2-3.5 | 0.49 |
| Melanoma-Other | 51 | 24 | 27 | 11-92 | 61.1 | 0.2-4.1 | 1.78 |
| Benign | 142 | 57 | 85 | 13-93 | 45.9 | n/a | n/a |
| Total | 302 | 138 | 164 | 11-93 | 53.7 | | |
| Melanoma | 160 | 81 | 79 | | | | |
| Benign | 142 | 57 | 85 | | | | |

From these 302 skin samples, 13,758 spectra were acquired. Of the 13,758 spectra, 4,197 were from melanoma, and 2,632 were from benign nevi. 5,203 additional spectra were acquired from adjacent dermis and epidermis stroma (non-relevant tissue background). Other spectra (1,768) include Bovine serum albumin digestion added to the plate as controls, as well as plate background areas (no tissue).

Training Data and Inclusion in Analysis.

For inclusion in the analysis, we required that each biopsy have pathology representative of invasive melanoma. Spectra collected from biopsies representing both superficial spreading and lentigo maligna type melanoma were combined to represent the invasive melanoma class and were compared to spectra from biopsies representing both benign junctional and intradermal nevi. A total of 2,146 mass spectra from 107 invasive melanoma biopsies (25 lentigo malgina, 82 superficial spreading) were compared to a total of 2,632 mass spectra from 119 benign biopsies. Further, 89 benign nevi samples (1599 spectra) were placed in the training set with 30 samples (578 spectra). For melanoma, 77 samples (1159 spectra) were in the training set, 29 samples (648 spectra) were in the test set, including 17 samples with clinical follow up that were explicitly included. These samples with clinical follow up underwent further surgery or chemotherapy. All samples in the training and test set were partitioned randomly except for the 17 melanoma samples that were in the test set.

Table 18 provides top-weighted peaks (m/z values) comprising the signature used for the determination of melanoma by mass spectrometry.

TABLE 18

Top-weighted peaks (m/z values).

| | | | | | | | | | |
|---|---|---|---|---|---|---|---|---|---|
| 1603.0 | 2154.7 | 1209.7 | 1541.9 | 1546.0 | 1793.2 | 1455.9 | 1168.7 | 1791.2 | 957.6 |
| 1122.6 | 1219.7 | 991.6 | 1187.7 | 1269.8 | 1526.9 | 925.5 | 906.5 | 1851.3 | 1078.6 |
| 1316.8 | 940.5 | 2306.9 | 1550.0 | 1691.1 | 2073.6 | 976.5 | 1378.8 | 1340.8 | 1080.7 |
| 1467.9 | 1253.7 | 982.5 | 1026.6 | 984.5 | 1334.8 | 1865.3 | 960.5 | 945.5 | 1529.9 |
| 1237.7 | 1312.8 | 1306.8 | 1496.9 | 919.5 | 1829.2 | 1291.8 | 1181.7 | 1601.0 | 1063.6 |
| 1621.0 | 1293.7 | 1640.1 | 1485.9 | 961.5 | 835.5 | 904.5 | 1314.8 | 1084.6 | 1992.5 |
| 1353.8 | 2026.5 | 1016.6 | 1250.7 | 1801.2 | 2042.5 | 1884.3 | 1552.0 | 1503.9 | 1089.6 |
| 1445.9 | 1694.1 | 1101.6 | 888.5 | 1107.7 | 1287.8 | 1198.7 | 998.5 | 1273.7 | 883.5 |
| 1784.1 | 1044.6 | 1065.6 | 893.6 | 1342.8 | 916.5 | 1568.0 | 924.5 | 1143.6 | 878.5 |
| 933.5 | 1358.8 | 1282.7 | 1583.0 | 1506.9 | 821.4 | 1336.8 | 1146.6 | 1619.0 | 882.5 |

In some embodiments, at least 3, 4, 5, 6, 7, 8, 9, or 10 peaks from Table 18 are useful for the determination of melanoma by mass spectrometry. In some embodiments, at least 11, 12, 13, 14, 15, 16, 17, 18, 19, or 20 peaks from Table 18 are useful for the determination of melanoma by mass spectrometry. In some embodiments, at least 21, 22, 23, 24, 25, 26, 27, 28, 29, or 30 peaks from Table 18 are useful for the determination of melanoma by mass spectrometry. In some embodiments, at least 31, 32, 33, 34, 35, 36, 37, 38, 39, or 40 peaks from Table 18 are useful for the determination of melanoma by mass spectrometry. In some embodiments, at least 41, 42, 43, 44, 45, 46, 47, 48, 49, or 50 peaks from Table 18 are useful for the determination of melanoma by mass spectrometry. In some embodiments, at least 51, 52, 53, 54, 55, 56, 57, 58, 59, or 60 peaks from Table 18 are useful for the determination of melanoma by mass spectrometry. In some embodiments, at least 61, 62, 63, 64, 65, 66, 67, 68, 69, or 70 peaks from Table 18 are useful for the determination of melanoma by mass spectrometry. In some embodiments, at least 71, 72, 73, 74, 75, 76, 77, 78, 79, or 80 peaks from Table 18 are useful for the determination of melanoma by mass spectrometry. In some embodiments, at least 81, 82, 83, 84, 85, 86, 87, 88, 89, or 90 peaks from Table 18 are useful for the determination of melanoma by mass spectrometry. In some embodiments, at least 91, 92, 93, 94, 95, 96, 97, 98, 99, or 100 peaks from Table 18 are useful for the determination of melanoma by mass spectrometry.

Machine Learning and Assay Accuracy, Sensitivity and Specificity.

Sample peak data were trained using a SVM with a linear kernel. Fivefold cross-validation was performed tuning over first 16 cost function (C) values. The final cost function (C) of the model was 0.1, as empirically determined by cross-validated accuracy. Spectrally, the developed model was accurate to 97.6%, correctly classifying 623/648 melanoma spectra, and 574/578 benign. Sensitivity for the assay at the spectral level is therefore 96.1% with a specificity of 99.3%. At the sample level, 58 of the 59 test samples classified correctly, with the criteria that 85% of all mass spectra must be correctly classified for the sample to be considered correct. This threshold is set slightly below the probability accuracy of the model fitting on itself, where we found ~93% probability for correct predictions in both benign and melanoma. Previous publications in the field have had less stringent requirements of 50% to 66% of individual mass spectra correctly classified for a sample to be considered correct. Using these criteria, we had only a single specimen fail to classify as melanoma, but even in this case, 70% of the spectra within the sample were correctly classified (16/23). Importantly, this indeterminate sample was not a true benign sample classified as melanoma, but a true melanoma where the sample did not meet our threshold. The inventors will continue to examine the stringency of this cutoff criteria to maximize the efficacy. The assay sensitivity for melanoma at the sample level is 96.5% and the specificity 100% with an accuracy of 98.3%.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of differentiating non-Spitzoid nevus from non-Spitzoid malignant melanoma, the method comprising:
    obtaining a mass spectrometric profile from a sample obtained from a subject; and
    identifying said sample as a non-Spitz nevus or non-Spitzoid malignant melanoma based on the similarities and differences between said mass spectrometric profile and a mass spectrometric profile or profiles obtained from a known normal, non-Spitz nevus and/or non-Spitzoid malignant melanoma sample.

2. A method of identifying non-Spitzoid malignant melanoma, the method comprising:
    obtaining a mass spectrometric profile from a sample obtained from a subject; and
    identifying said sample as a non-Spitzoid malignant melanoma if the mass spectrometric profile from the sample is similar to a mass spectrometric profile obtained from a known non-Spitzoid malignant melanoma sample.

3. The method of claim 1, wherein the sample is a skin lesion sample.

4. The method of claim 3, wherein the skin lesion sample comprises melanocytic components.

5. The method of claim 1, wherein the mass spectrometric profile comprises one or more peaks at about m/z 1955, about m/z 1199, about m/z 1184, about m/z 1412, or about m/z 2216.

6. The method of claim 1, wherein the profile comprises a plurality of molecules.

7. The method of claim 6, wherein the molecules comprise at least one protein, at least one peptide, at least one lipid, at least one metabolite, or a combination thereof.

8. The method of claim 1, further comprising the step of administering to the subject an anti-cancer agent.

9. The method of claim 1, wherein said anti-cancer agent comprises chemotherapy, immunotherapy, toxin therapy, radiotherapy, or a combination thereof.

10. The method of claim 1, wherein said mass spectrometry comprises secondary ion mass spectrometry, electrospray mass spectrometry, or desorption electrospray ionization.

11. The method of claim 1, further comprising obtaining said sample from said subject.

12. The method of claim 1, further comprising performing a mass spectrometric analysis of a known non-Spritz nevi and/or non-Spitzoid malignant melanoma lesion.

13. The method of claim 1, further comprising performing histologic analysis on said sample.

14. The method of claim 1, further comprising determining said subject's survival based on said identification.

15. The method of claim 1, further comprising performing immunohistochemical analysis on said sample.

16. A method of identifying non-Spitzoid malignant melanoma, the method comprising:
    obtaining a mass spectrometric profile from a sample obtained from a subject, wherein the mass spectrometric profile comprises one or more peaks at about m/z 1955, about m/z 1199, about m/z 1184, about m/z 1412, or about m/z 2216;
    identifying said sample as a non-Spitzoid malignant melanoma if the mass spectrometric profile from the sample is similar to a mass spectrometric profile obtained from a known non-Spitzoid malignant melanoma sample; and
    administering to a subject an anti-cancer agent.

17. The method of claim 16, further comprising the step of obtaining the skin lesion sample from the subject.

18. The method of claim 16, wherein said mass spectrometry comprises secondary ion mass spectrometry, laser desorption mass spectrometry, matrix assisted laser desorption/ionization mass spectrometry, electrospray mass spectrometry, or desorption electrospray ionization.

19. The method of claim 16, wherein the anti-cancer agent comprises chemotherapy, immunotherapy, toxin therapy, radiotherapy, or a combination thereof.

20. A method of identifying melanoma, the method comprising:
    obtaining a mass spectrometric profile from a sample obtained from a subject; and
    identifying similarities and differences between said mass spectrometric profile to a profile obtained from a known normal, non-Spitzoid nevi and/or non-Spitzoid malignant melanoma sample, wherein the mass spectrometric profile comprises peaks at about m/z 1955, about m/z 1199, about m/z 1184, about m/z 1412, or about m/z 2216; and
    identifying said sample as a non-Spitzoid malignant melanoma if the mass spectrometric profile from the sample is similar to the mass spectrometric profile obtained from a known non-Spitzoid malignant melanoma.

\* \* \* \* \*